(12) United States Patent
Andersen et al.

(10) Patent No.: US 10,071,963 B2
(45) Date of Patent: Sep. 11, 2018

(54) POLYMORPHIC FORM OF N-[2-(6-FLUORO-1H-INDOL-3-YL)ETHYL]-3-(2,2,3,3-TETRAFLUOROPOPOXY)BENZYLAMINE HYDROCHLORIDE FOR THE TREATMENT OF ALZHEIMER'S DISEASE

(71) Applicant: H. Lundbeck A/S, Valby (DK)

(72) Inventors: Kristine Birklund Andersen, Stenløse (DK); Michael Harold Rock, Frederiksberg C (DK); Heidi Lopez De Diego, Nærum (DK); Frans Dennis Therkelsen, Holbæk (DK)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 15/323,426

(22) PCT Filed: Jul. 3, 2015

(86) PCT No.: PCT/EP2015/065176
§ 371 (c)(1),
(2) Date: Jan. 2, 2017

(87) PCT Pub. No.: WO2016/001398
PCT Pub. Date: Jan. 7, 2016

(65) Prior Publication Data
US 2017/0152227 A1    Jun. 1, 2017

(30) Foreign Application Priority Data

Jul. 4, 2014  (DK) ................. 2014 00369

(51) Int. Cl.
*A61K 31/4045* (2006.01)
*C07D 209/16* (2006.01)
*C07D 209/14* (2006.01)
*A61K 45/06* (2006.01)

(52) U.S. Cl.
CPC ........ *C07D 209/16* (2013.01); *A61K 31/4045* (2013.01); *A61K 45/06* (2013.01); *C07D 209/14* (2013.01); *C07B 2200/13* (2013.01)

(58) Field of Classification Search
None
See application file for complete search history.

(56) References Cited

U.S. PATENT DOCUMENTS 7,157,488 B2    1/2007   Chen et al.

FOREIGN PATENT DOCUMENTS

| CN | 1610547 A | 4/2005 |
|---|---|---|
| WO | WO 2011/076212 | 6/2011 |
| WO | WO-2014/037532 A1 | 3/2014 |
| WO | WO 2016/078587 | 5/2016 |

OTHER PUBLICATIONS

Wolfgang Beckmann, Organic Process Research & Development, 2000, 4, 372-383.*
Caira, M.R. (1998) "Crystalline Polymorphism of Organic Compounds," Topics in Current Chemistry 198:163-208.
International Search Report PCT/EP2015/0065176 (WO 2016/001398) (dated 2015) (4 pages).
Written Opinion of the International Searching Authority PCT/EP2015/065176 (WO 2016/001398) (dated 2015) (6 pages).
CN 1610547A (Computer-Generated English Translation).
WO 2016/078587 (Computer-Generated English Translation).

* cited by examiner

*Primary Examiner* — Alicia L Otton
(74) *Attorney, Agent, or Firm* — Wilmer Cutler Pickering Hale and Dorr LLP

(57) ABSTRACT

The present invention relates to a novel polymorphic form of N-[2-(6-fluoro-1H-indol-3-yl)ethyl]-3-(2,2,3,3-tetrafluoropropoxy)benzylamine hydrochloride.

21 Claims, 11 Drawing Sheets

Polymorphic form I:

Polymorphic form II:

POLYMORPHIC FORM OF N-[2-(6-FLUORO-1H-INDOL-3-YL)ETHYL]-3-(2,2,3,3-TETRAFLUOROPROPOXY)BENZYLAMINE HYDROCHLORIDE FOR THE TREATMENT OF ALZHEIMER'S DISEASE

CROSS REFERENCE TO RELATED APPLICATIONS

This application is a § 371 Application of PCT/EP2015/065176 (filed on Jul. 3, 2015; pending), which application claims priority to Denmark Patent Application No. PA201400369 (filed on Jul. 4, 2014).

FIELD OF THE INVENTION

The present invention relates to a novel polymorphic form of N-[2-(6-fluoro-1Hindol-3-yl)ethyl]-3-(2,2,3,3-tetrafluoropropoxy)benzylamine hydrochloride.

BACKGROUND OF THE INVENTION

The incidence of Alzheimer's disease is expected to increase through the year 2050 with an estimated prevalence of 11 to 16 million cases. Currently, two classes of medications are FDA approved for managing symptoms of Alzheimer's disease—acetylcholinesterase inhibitors (AChEIs) and an N-methyl-D-aspartase (NMDA) receptor antagonist. AChEIs are commonly used as initial treatment on diagnosis. The AChEIs—donepezil, rivastigmine, galantamine, and tacrine—are indicated for mild-to-moderate Alzheimer's disease; only donepezil is approved for the severe stage.

AChEIs do not help everyone who has Alzheimer's disease and in fact are not efficacious in many patients. Considering that AChEIs and memantine have only a modest symptomatic effect, and cannot prevent Alzheimer's disease decline and slow disease progression, there is a high unmet need for more effective symptomatic treatments and for a disease modifying/slowing therapies.

The use of selective 5-HT6 receptor antagonists to treat cognitive dysfunction has been suggested and is based on several lines of reasoning. For example, selective 5-HT6 receptor antagonists have been shown to modulate cholinergic and glutamatergic neuronal function. The activity of selective 5-HT6 receptor antagonists has been demonstrated in animal models of cognitive function. Since the disclosure of the first selective 5-HT6 receptor antagonists, there have been several reports on the activity of these selective compounds in in-vivo models of cognitive function. N-[2-(6-fluoro-1H-indol-3-yl)ethyl]-3-(2,2,3,3-tetrafluoropropoxy)benzylamine, CAS number 467458-02-2, (herein also referred to as "Lu AE58054") is a 5-HT6 receptor antagonist and its chemical structure is depicted below:

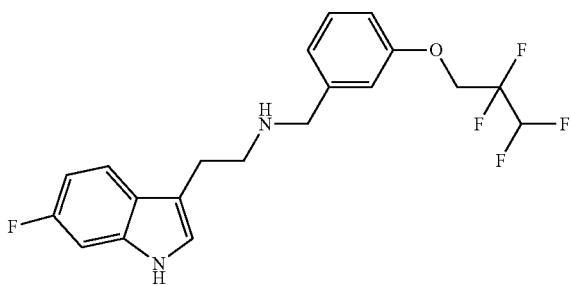

Lu AE58054

The synthesis of N-[2-(6-fluoro-1H-indol-3-yl)ethyl]-3-(2,2,3,3-tetrafluoropropoxy)benzylamine, its use for the treatment of Alzheimer's disease, and pharmaceutical compositions comprising this compound are disclosed in U.S. Pat. No. 7,157,488 ("the '488 patent"). The '488 patent further describes the preparation of the hydrochloride salt of N-[2-(6-fluoro-1H-indol-3-yl)ethyl]-3-(2,2,3,3-tetrafluoropropoxy)benzylamine.

N-[2-(6-fluoro-1H-indol-3-yl)ethyl]-3-(2,2,3,3-tetrafluoropropoxy)benzylamine can be produced according to the method described in WO 11/76212.

By using the methods in the '488 patent and in WO 11/76212, the N-[2-(6-fluoro-1H-indol-3-yl)ethyl]-3-(2,2,3,3-tetrafluoropropoxy)benzylamine hydrochloride is obtained as a solid.

Pharmaceutical solids can exist in amorphous, glass or crystalline states. Furthermore crystalline materials can be found as hydrates or other solvates. If such a compound can exist in more than one crystalline arrangement (polymorphic form) the compound is said to show polymorphism.

In order to be able to provide an active pharmaceutical ingredient of high and reproducible quality and with well-defined biological activity, it is desirable to have the active pharmaceutical ingredient in the most thermodynamically stable form.

The inventors of the present invention have found a new and thermodynamically stable form of the hydrochloride salt of N-[2-(6-fluoro-1H-indol-3-yl)ethyl]-3-(2,2,3,3-tetrafluoropropoxy)benzylamine.

SUMMARY OF THE INVENTION

The present invention relates to polymorphic form III of N-[2-(6-fluoro-1H-indol-3-yl)ethyl]-3-(2,2,3,3-tetrafluoropropoxy)benzylamine hydrochloride.

The invention further relates to a process preparing polymorphic form III of N-[2-(6-fluoro-1H-indol-3-yl)ethyl]-3-(2,2,3,3-tetrafluoropropoxy)benzylamine hydrochloride comprising:

a. capturing polymorphic form III of N-[2-(6-fluoro-1H-indol-3-yl)ethyl]-3-(2,2,3,3-tetrafluoropropoxy)benzylamine hydrochloride from a suspension of N-[2-(6-fluoro-1H-indol-3-yl)ethyl]-3-(2,2,3,3-tetrafluoropropoxy)benzylamine in an organic solvent selected from the list of acetonitrile, proprionitrile, acetone, methanol, ethanol, toluene and xylenes (ortho, meta or para) or a mixture thereof, at a temperature below 60° C.

The invention further relates to a process for preparing polymorphic form III of N-[2-(6-fluoro-1H-indol-3-yl)ethyl]-3-(2,2,3,3-tetrafluoropropoxy)benzylamine hydrochloride comprising:

a. adding polymorphic form I, form II, amorphous or a mixture of the forms of N-[2-(6-fluoro-1H-indol-3-yl)ethyl]-3-(2,2,3,3-tetrafluoropropoxy)benzylamine hydrochloride to an organic solvent selected from the list of acetonitrile, proprionitrile, acetone, methanol, ethanol, toluene and xylenes (ortho, meta or para) or a mixture thereof, at a temperature below 60° C. to produce a suspension;

b. capturing polymorphic form III of N-[2-(6-fluoro-1H-indol-3-yl)ethyl]-3-(2,2,3,3-tetrafluoropropoxy)benzylamine hydrochloride.

The invention further relates to a process for preparing polymorphic form III of N-[2-(6-fluoro-1H indol-3-yl)ethyl]-3-(2,2,3,3-tetrafluoropropoxy)benzylamine hydrochloride comprising:

a. seeding a suspension of N-[2-(6-fluoro-1H-indol-3-yl)ethyl]-3-(2,2,3,3-tetrafluoropropoxy)benzylamine hydrochloride in an organic solvent selected from the list of acetonitrile, proprionitrile, acetone, methanol, ethanol, toluene and xylenes (ortho, meta or para) or a mixture thereof, at a temperature below 60° C. with polymorphic form III of N-[2-(6-fluoro-1H-indol-3-yl)ethyl]-3-(2,2,3,3-tetrafluoropropoxy)benzylamine hydrochloride;

b. capturing polymorphic form III of N-[2-(6-fluoro-1H-indol-3-yl)ethyl]-3-(2,2,3,3-tetrafluoropropoxy)benzylamine hydrochloride.

The invention further relates to a process for preparing polymorphic form III of N-[2-(6-fluoro-1H-indol-3-yl)ethyl]-3-(2,2,3,3-tetrafluoropropoxy)benzylamine hydrochloride comprising:

a. adding polymorphic form I, form II, amorphous or a mixture of the forms of N-[2-(6-fluoro-1H-indol-3-yl)ethyl]-3-(2,2,3,3-tetrafluoropropoxy)benzylamine hydrochloride to an organic solvent selected from the list of acetonitrile, proprionitrile, acetone, methanol, ethanol, heptane, toluene and xylenes (ortho, meta or para) or a mixture thereof, at a temperature below 60° C. to produce a suspension;

b. seeding with polymorphic form III of N-[2-(6-fluoro-1H-indol-3-yl)ethyl]-3-(2,2,3,3-tetrafluoropropoxy)benzylamine hydrochloride at a temperature below 60° C.;

c. capturing polymorphic form III of N-[2-(6-fluoro-1H-indol-3-yl)ethyl]-3-(2,2,3,3-tetrafluoropropoxy)benzylamine hydrochloride.

The invention further relates to polymorphic form III of N-[2-(6-fluoro-1H-indol-3-yl)ethyl]-3-(2,2,3,3-tetrafluoropropoxy)benzylamine hydrochloride for use as a medicament, a pharmaceutical composition comprising polymorphic form III of N-[2-(6-fluoro-1H-indol-3-yl)ethyl]-3-(2,2,3,3-tetrafluoropropoxy)benzylamine hydrochloride and a method of treating Alzheimer's disease as adjunctive therapy to acetylcholinesterase treatment comprising administering an effective daily dose of polymorphic form III of N-[2-(6-fluoro-1H-indol-3-yl)ethyl]-3-(2,2,3,3-tetrafluoropropoxy)benzylamine hydrochloride to a patient in need of such treatment.

DETAILED DESCRIPTION OF THE INVENTION

Previous to the present invention; two polymorphic modifications of the N-[2-(6-fluoro-1H-indol-3-yl)ethyl]-3-(2,2,3,3-tetrafluoropropoxy)benzylamine hydrochloride were known. Polymorphic form I which was found to be the thermodynamically stable form at low temperature (below about 60° C.) and polymorphic form II which is the thermodynamically stable form at high temperature (above about 60° C.). Polymorphic form II has a melting point, as determined by Differential scanning calorimetry (DSC) at 171° C. Polymorphic form I transforms into polymorphic form II upon heating in the temperature range 120-140° C., thus a melting point of polymorphic form I could not be determined. The crystal structures of both polymorphic forms were determined using single crystal X-ray analysis. The structural parameters are given in Table 1 below:

TABLE 1

Table 1 - Structural parameters of polymorphic form I and form II of N-[2-(6-fluoro-1H-indol-3-yl)ethyl]-3-(2,2,3,3-tetrafluoropropoxy)benzylamine hydrochloride.

| Polymorphic form I | Polymorphic form II |
|---|---|
| $C_{20}H_{20}F_5N_2O^+ \cdot Cl^-$ | $C_{20}H_{20}F_5N_2O^+ \cdot Cl^-$ |
| $M_r$ = 434.83 | $M_r$ = 434.83 |
| T = 298 (2) K | T = 298 (2) K |
| Monoclinic, $P2_1$ | Orthorhombic, Pbca |
| a = 7.3776 (3) Å | a = 10.529 (3) Å |
| b = 7.0709 (3) Å | b = 9.569 (3) Å |
| c = 38.3480 (19) Å | c = 41.398 (10) Å |
| beta = 94.103 (1)° | — |
| V = 1995.34 (15) Å$^3$ | V = 4171 (2) Å$^3$ |
| Z = 4 | Z = 8 |
| $D_x$ = 1.447 Mg m$^{-3}$ | $D_x$ = 1.385 Mg m$^{-3}$ |

Figure 6:
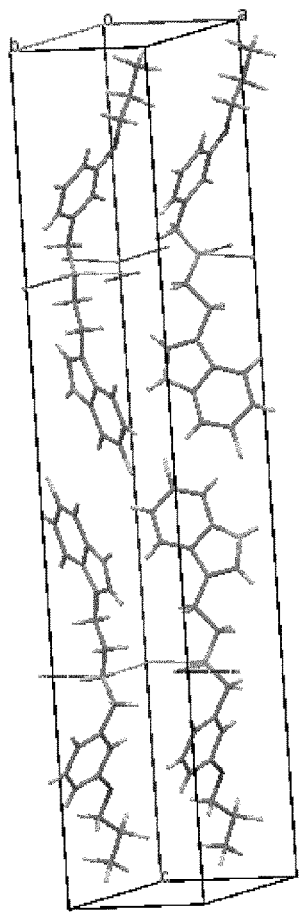
FIG. 6: Shows crystal packing of polymorphic form I and form II of N-[2-(6-fluoro-1H-indol-3-yl)ethyl]-3-(2,2,3,3-tetrafluoropropoxy)benzylamine hydrochloride.
Figure 6:
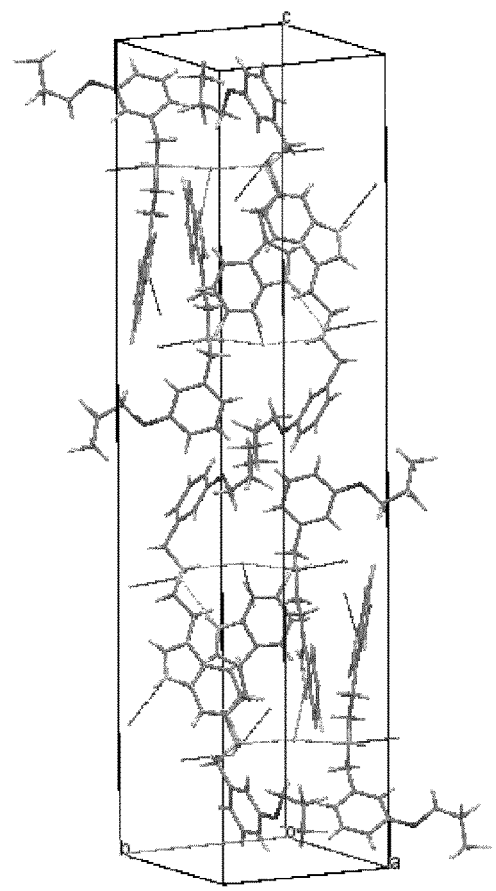

The crystal packing differs significantly in the two polymorphic forms (FIG. 6).

Crystallization experiments have been performed in the search for other polymorphic modifications without success. All experiments resulted in polymorphic form I and form II, depending on the temperature. It was therefore surprising to find a new and thermodynamically more stable form that based on DSC is very similar to polymorphic form I (it also transforms into polymorphic form II by heating in the temperature range 120° C.-140° C.), and has many low-angle reflections in common with polymorphic form I in X-ray powder diffractogram (XRPD), but also differ significantly in other reflections.

Despite previous unsuccessful attempts to find new polymorphic forms of N-[2-(6-fluoro-1H-indol-3-yl)ethyl]-3-(2,2,3,3-tetrafluoropropoxy)benzylamine hydrochloride, the inventors of the present invention have found a way to produce a new polymorphic form of N-[2-(6-fluoro-1H-indol-3-yl)ethyl]-3-(2,2,3,3-tetrafluoropropoxy)benzylamine hydrochloride, in the following referred to as polymorphic form III.

It has been found that in the temperature range where polymorphic form III of N-[2-(6-fluoro-1H-indol-3-yl)ethyl]-3-(2,2,3,3-tetrafluoropropoxy)benzylamine hydrochloride is the thermodynamically stable polymorphic form, it is easier to produce polymorphic form I and II of N-[2-(6-fluoro-1H-indol-3-yl)ethyl]-3-(2,2,3,3-tetrafluoropropoxy)benzylamine hydrochloride. In summary polymorphic form I and form II of N-[2-(6-fluoro-1H-indol-3-yl)ethyl]-3-(2,2,3,3-tetrafluoropropoxy)benzylamine hydrochloride have a kinetic advantage over polymorphic form III which is the thermodynamically stable form making this polymorphic form more difficult to produce.

Polymorphic form III is particular advantageous in that it is the most thermodynamically stable form of N-[2-(6-fluoro-1H-indol-3-yl)ethyl]-3-(2,2,3,3-tetrafluoropropoxy)benzylamine hydrochloride.

The present invention is further described in the embodiments 1 to 42 (E(1) to E(42)) below:

E(1): Polymorphic form III of N-[2-(6-fluoro-1H-indol-3-yl)ethyl]-3-(2,2,3,3-tetrafluoropropoxy)benzylamine hydrochloride.

E(2): The polymorphic form according to (E1) characterized by an X-Ray powder diffractogram showing peaks at the following 2θ-angles: 4.63°, 6.94°, 13.89°, 17.26° and 19.97°.

E(3): The polymorphic form according to (E2) further characterized by an X-Ray powder diffractogram showing peaks at the following 2θ-angles: 4.63°, 6.94°, 13.89°, 17.26°, 18.95°, 19.97°, 22.53° and 23.65°.

E(4): The polymorphic form according to (E3) further characterized by an X-Ray powder diffractogram showing peaks at the following 2θ-angles: 4.63°, 6.94°, 13.89°, 17.26°, 18.07°, 18.49°, 18.95°, 19.47°, 19.97°, 20.53°, 21.83°, 22.53°, 23.27°, 23.65° and 28.91°.

Figure 1:
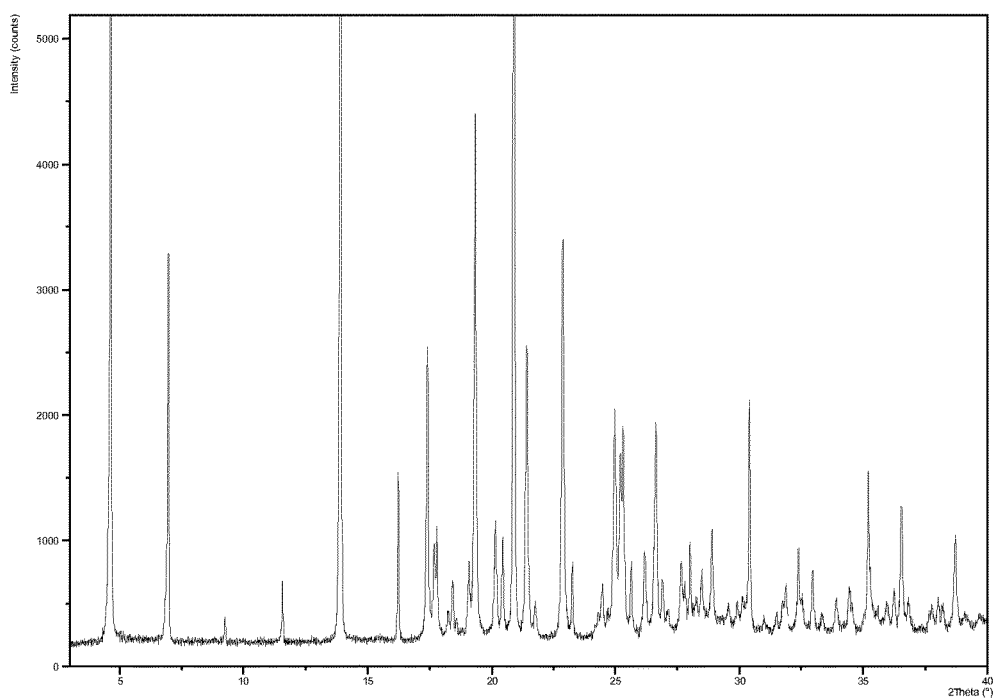
FIG. 1: X-ray powder diffractogram of polymorphic form I of N-[2-(6-fluoro-1H-indol-3-yl)ethyl]-3-(2,2,3,3-tetrafluoropropoxy)benzylamine hydrochloride.
Figure 2:
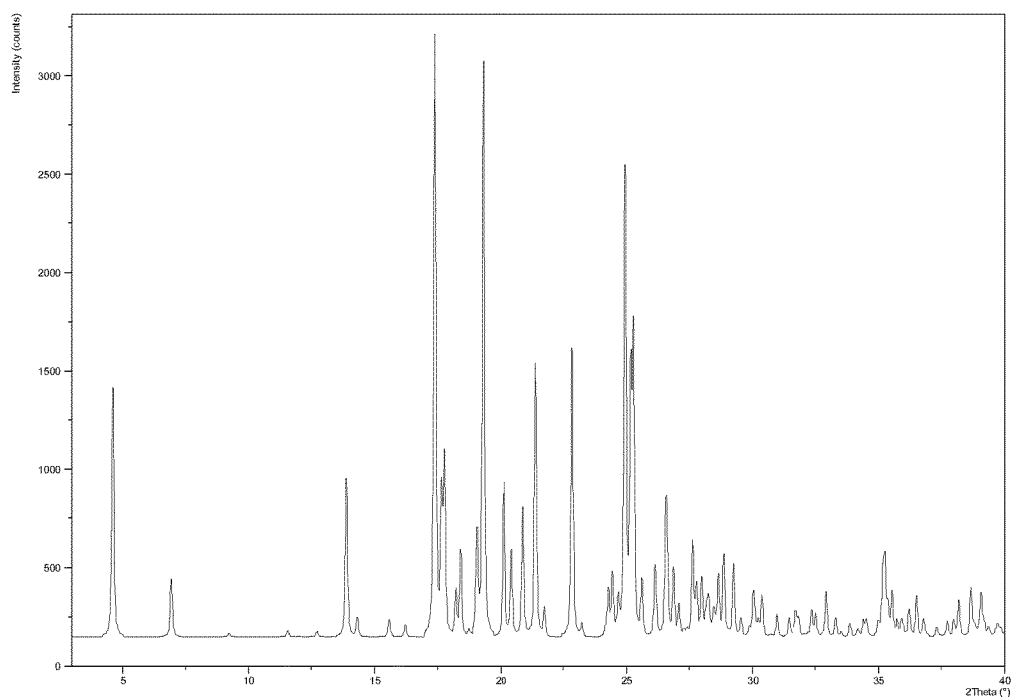
FIG. 2: X-ray powder diffractogram calculated from the crystal structure of polymorphic form I.
Figure 3:
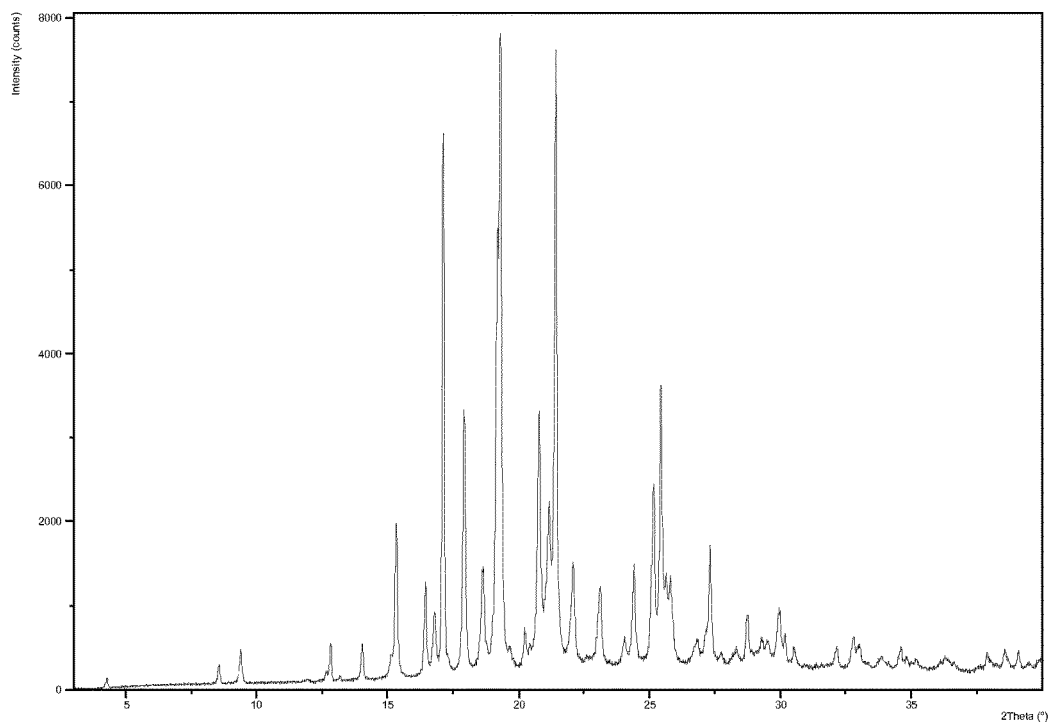
FIG. 3: X-ray powder diffractogram of polymorphic form II of N-[2-(6-fluoro-1H-indol-3-yl)ethyl]-3-(2,2,3,3-tetrafluoropropoxy)benzylamine hydrochloride.
Figure 4:
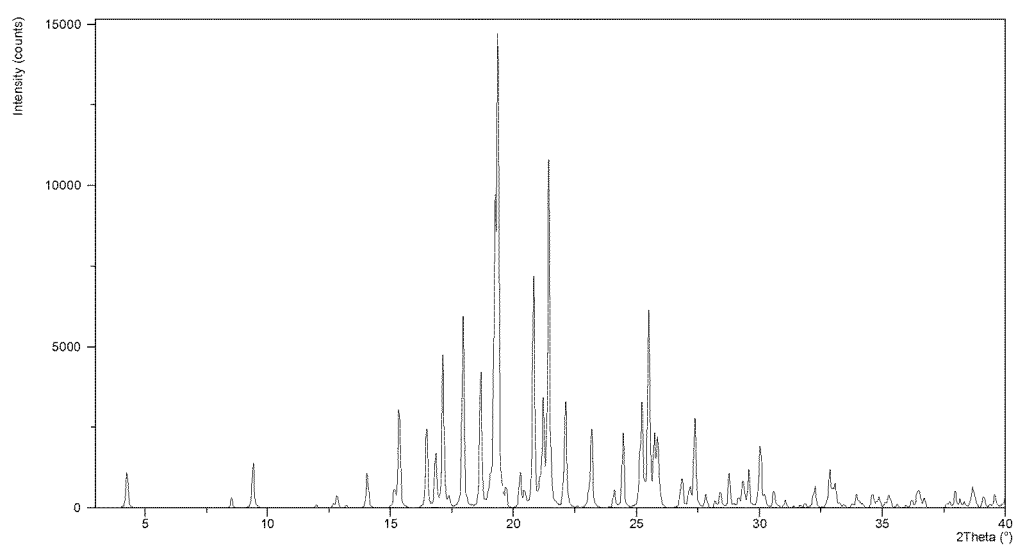
FIG. 4: X-ray powder diffractogram calculated from the crystal structure of polymorphic form II.
Figure 5:
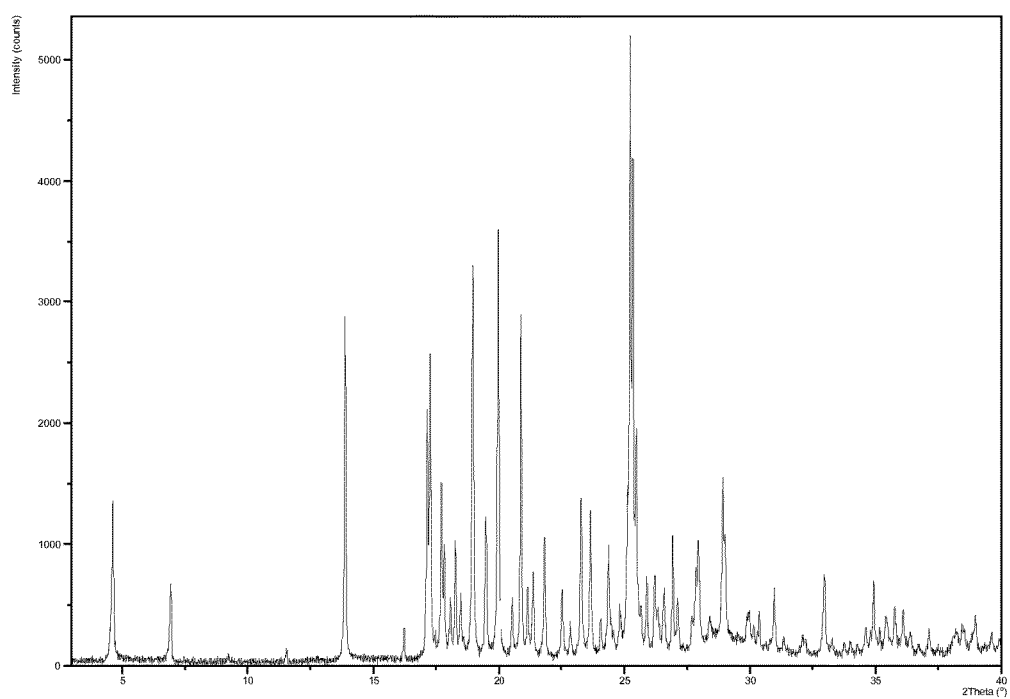
FIG. 5: X-ray powder diffractogram of polymorphic form III of N-[2-(6-fluoro-1H-indol-3-yl)ethyl]-3-(2,2,3,3-tetrafluoropropoxy)benzylamine hydrochloride.

E(5): The polymorphic form according to (E1), wherein said compound exhibits an X-Ray powder diffractogram as shown in FIG. 5.

E(6): A process for preparing polymorphic form III of N-[2-(6-fluoro-1H-indol-3-yl)ethyl]-3-(2,2,3,3-tetrafluoropropoxy)benzylamine hydrochloride comprising:
  capturing polymorphic form III of N-[2-(6-fluoro-1H-indol-3-yl)ethyl]-3-(2,2,3,3-tetrafluoropropoxy)benzylamine hydrochloride from a suspension of N-[2-(6-fluoro-1H-indol-3-yl)ethyl]-3-(2,2,3,3-tetrafluoropropoxy)benzylamine hydrochloride in an organic solvent selected from the list of acetonitrile, proprionitrile, acetone, methanol, ethanol, toluene and xylenes (ortho, meta or para) or a mixture thereof, at a temperature below 60° C.

E(7): A process for preparing polymorphic form III of N-[2-(6-fluoro-1H-indol-3-yl)ethyl]-3-(2,2,3,3-tetrafluoropropoxy)benzylamine hydrochloride comprising:
  a) adding polymorphic I, form II, amorphous or a mixture of the forms of N-[2-(6-fluoro-1H-indol-3-yl)ethyl]-3-(2,2,3,3-tetrafluoropropoxy)benzylamine hydrochloride to an organic solvent selected from the list of acetonitrile, proprionitrile, acetone, methanol, ethanol, toluene and xylenes (ortho, meta or para) or a mixture thereof, at a temperature below 60° C. to produce a suspension;
  b) capturing polymorphic form III of N-[2-(6-fluoro-1H-indol-3-yl)ethyl]-3-(2,2,3,3-tetrafluoropropoxy)benzylamine hydrochloride.

E(8): A process for preparing polymorphic form III of N-[2-(6-fluoro-1H-indol-3-yl)ethyl]-3-(2,2,3,3-tetrafluoropropoxy)benzylamine hydrochloride comprising:
  a) seeding a suspension of N-[2-(6-fluoro-1H-indol-3-yl)ethyl]-3-(2,2,3,3-tetrafluoropropoxy)benzylamine hydrochloride in an organic solvent selected from the list of acetonitrile, proprionitrile, acetone, methanol, ethanol, toluene and xylenes (ortho, meta or para) or a mixture thereof, at a temperature below 60° C. with polymorphic form III of N-[2-(6-fluoro-1H-indol-3-yl)ethyl]-3-(2,2,3,3-tetrafluoropropoxy)benzylamine hydrochloride;
  b) capturing polymorphic form III of N-[2-(6-fluoro-1H-indol-3-yl)ethyl]-3-(2,2,3,3-tetrafluoropropoxy)benzylamine hydrochloride.

E(9): A process for preparing polymorphic form III of N-[2-(6-fluoro-1H-indol-3-yl)ethyl]-3-(2,2,3,3-tetrafluoropropoxy)benzylamine hydrochloride comprising:
  a) adding polymorphic I, form II, amorphous or a mixture of the forms of N-[2-(6-fluoro-1H-indol-3-yl)ethyl]-3-(2,2,3,3-tetrafluoropropoxy)benzylamine hydrochloride to an organic solvent selected from the list of acetonitrile, proprionitrile, acetone, methanol, ethanol, heptane, toluene and xylenes (ortho, meta or para) or a mixture thereof, at a temperature below 60° C. to produce a suspension;
  b) seeding with polymorphic form III of N-[2-(6-fluoro-1H-indol-3-yl)ethyl]-3-(2,2,3,3-tetrafluoropropoxy)benzylamine hydrochloride at a temperature below 60° C.;
  c) capturing polymorphic form III of N-[2-(6-fluoro-1H-indol-3-yl)ethyl]-3-(2,2,3,3-tetrafluoropropoxy)benzylamine hydrochloride.

E(10): The process according to any of the (E6) to (E9) wherein the mixture of organic solvents is such that crystallization occurs below 60° C.

E(11): The process according to any of the (E6) to (E9), wherein the organic solvent is a mixture of acetone and heptane in the ratio 1:4.

E(12): The process according to any of the (E6) to (E9), wherein the organic solvent is a mixture of methanol and toluene in the ratio 1:4.

E(13): A compound according to any of the (E1) to (E5) for use as a medicament.

E(14): A pharmaceutical composition comprising a compound according to any of the (E1) to (E5).

E(15): The pharmaceutical formulation according to (E14) comprising pharmaceutically acceptable carriers or diluents.

E(16): A method of treating Alzheimer's disease as adjunctive therapy to acetylcholinesterase treatment comprising administering an effective daily dose of a compound according to any of the E(1) to E(5) to a patient in need of such treatment.

E(17): The method according to E(16), wherein the effective daily dose administered to the patient of said compound is between about 5 and about 120 mg.

E(18): The method according to E(16), wherein the effective daily dose administered to the patient of said compound is between about 30 and about 60 mg E(19): The method of according to any of E(16) to E(18), wherein the acetylcholinesterase inhibitor is donepezil.

E(20): The method according to any of E(16) to E(18), wherein the acetylcholinesterase inhibitor is rivastigmine.

E(21): The method according to any of E(16) to E(18), wherein the acetylcholinesterase inhibitor is galantamine.

E(22): The method according to any of E(16) to E(18), wherein the acetylcholinesterase inhibitor is tacrine.

E(23): A method of treating a disease or disorder selected from dementia in Parkinson's disease,
Huntington's chorea and Down's syndrome comprising administering an effective daily dose of a compound according to any of E(1) to E(5)to a patient in need of such treatment E(24): A method of treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis comprising administering an effective daily dose of a compound according to any of E(1) to E(5) to a patient in need of such treatment E(25): A compound according to any of E(1) to E(5) for use in treating Alzheimer's disease as adjunctive therapy to acetylcholinesterase treatment.

E(26): The compound according to E(25), wherein the dose of said compound is between about 5 and about 120 mg.

E(27): The compound according to E(25), wherein the dose of said compound is between about 30 and about 60 mg.

E(28): The compound according to any of E(25)-E(27), wherein the acetylcholinesterase inhibitor is donepezil.

E(29): The compound according to any of E(25)-E(27), wherein the acetylcholinesterase inhibitor is rivastigmine.

E(30): The compound according to any of E(25)-E(27), wherein the acetylcholinesterase inhibitor is galantamine.

E(31): The compound according to any of E(25)-E(27), wherein the acetylcholinesterase inhibitor is tacrine.

E(32): A compound according to any of E(1)-E(5) for use in treating a disease or disorder selected from dementia in Parkinson's disease, Huntington's chorea and Down's syndrome.

E(33): A compound according to any of E(1)-E(5) for use in treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis.

E(34): Use of a compound according to any of E(1)-E(5) for the manufacture of a medicament for treating Alzheimer's disease as adjunctive therapy to acetylcholinesterase treatment.

E(35): The use according E(34), wherein the dose of said compound is between about 5 and about 120 mg.

E(36): The use according to E(34), wherein the dose of said compound is between about 30 and about 60 mg.

E(37): The use according to any of E(34) to E(36), wherein the acetylcholinesterase inhibitor is donepezil.

E(38): The use according to any of E(34) to E(36), wherein the acetylcholinesterase inhibitor is rivastigmine.

E(39): The use according to any of E(34) to E(36), wherein the acetylcholinesterase inhibitor is galantamine.

E(40): The use according to any of E(34) to E(36), wherein the acetylcholinesterase inhibitor is tacrine.

E(41): Use of a compound according to any of E(1) to E(5) for the manufacture of a medicament for treating a disease or disorder selected from dementia in Parkinson's disease, Huntington's chorea and Down's syndrome.

E(42): Use of a compound according to any of E(1) to E(5) for the manufacture of a medicament for treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis.

E(43): The process according to any of E(6) to E(10) wherein the suspension is prepared at a temperature about 50° C., such as 45-55° C.

E(44): The process according to any of E(6) to E(10) wherein the suspension is prepared at a temperature below 50° C.

E(45): The polymorphic form according to (E1) characterized by an FTIR spectrum having relative strong band intensity at the following band positions [cm$^{-1}$]: 3426, 1586, 1089, 762 and a shoulder at 1099 cm$^{-1}$.

Figure 10:
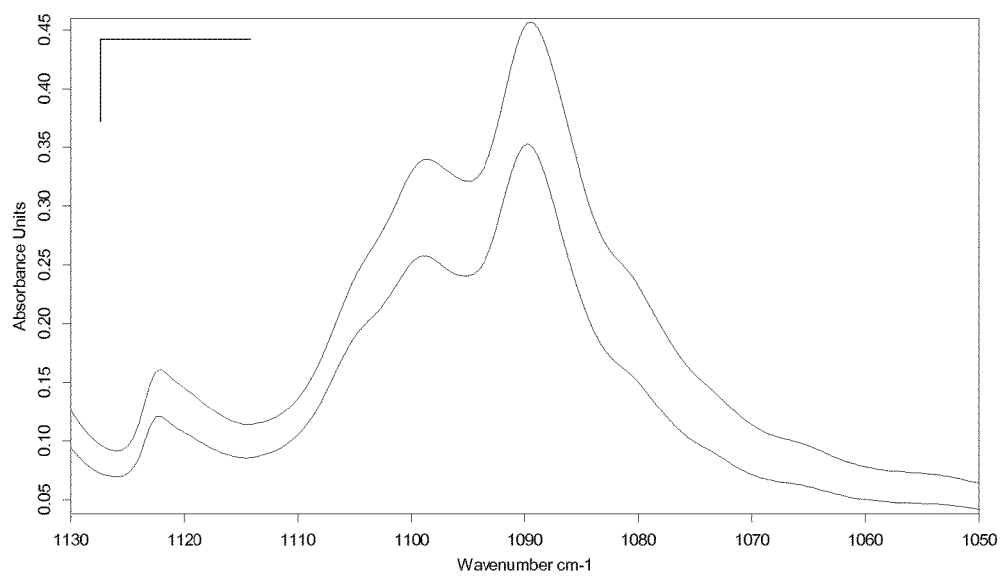
FIG. 10: FTIR spectra of two batches of polymorphic form III shown in the spectral region 1130-1050 cm$^{-1}$.
Figure 11:
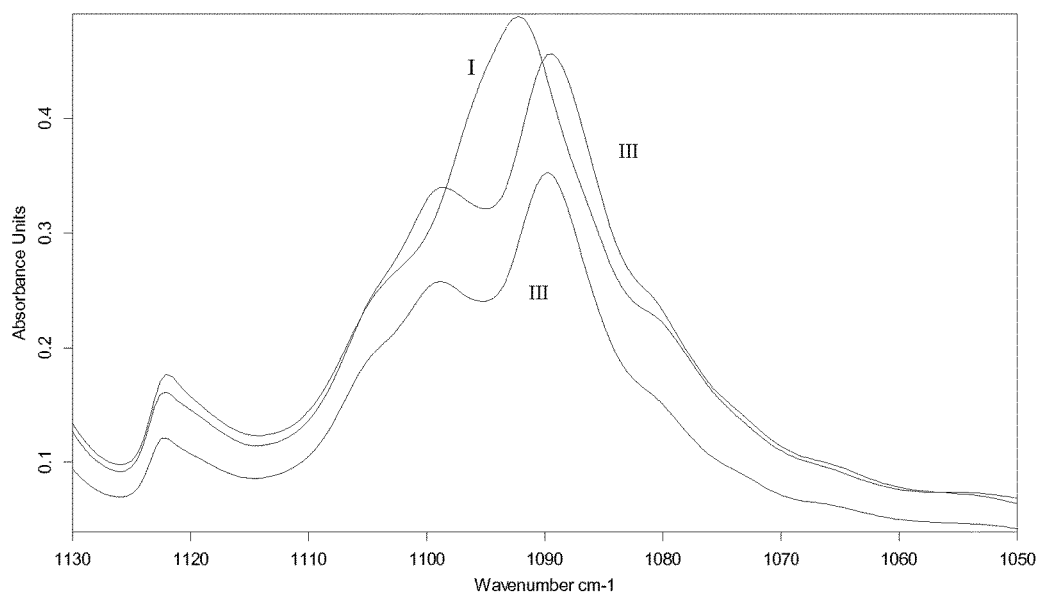
FIG. 11: FTIR spectra of two batches of polymorphic form III (marked with "III") and one spectrum of polymorphic form I (marked with "I") shown in the spectral region 1130-1050 cm$^{-1}$.

E(46): The polymorphic form according to (E1) characterized by an FTIR spectrum in the spectral region 1130-1050 cm$^{-1}$ as shown in FIG. 10.

E(47): A pharmaceutical composition prepared from polymorphic form III of N-[2-(6-fluoro-1H-indol-3-yl)ethyl]-3-(2,2,3,3-tetrafluoropropoxy)benzylamine hydrochloride.

E(48): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an X-Ray powder diffractogram showing peaks at the following 2θ-angles: 4.63°, 6.94°, 13.89°, 17.26° and 19.97°.

E(49): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an X-Ray powder diffractogram showing peaks at the following 2θ-angles: 4.63°, 6.94°, 13.89°, 17.26°, 18.95°, 19.97°, 22.53° and 23.65°.

E(50): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an X-Ray powder diffractogram showing peaks at the following 2θ-angles:: 4.63°, 6.94°, 13.89°, 17.26°, 18.07°, 18.49°, 18.95°, 19.47°, 19.97°, 20.53°, 21.83°, 22.53°, 23.27°, 23.65° and 28.91°.

E(51): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an X-Ray powder diffractogram as shown in FIG. 5

E(52): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an FTIR spectrum having strong band intensity at the following band positions [cm$^{-1}$]: 3426, 1586, 1089, 762 and a shoulder at 1099 cm$^{-1}$.

E(53): A pharmaceutical composition prepared from polymorphic form III of N-[2-(6-fluoro-1H-indol-3-yl)ethyl]-3-(2,2,3,3-tetrafluoropropoxy)benzylamine hydrochloride characterized by an FTIR spectrum in the spectral region 1130-1050 cm$^{-1}$ as shown in FIG. 10.

Definitions

N-[2-(6-fluoro-1H-indol-3-yl)ethyl]-3-(2,2,3,3-tetrafluoropropoxy)benzylamine is "Lu AE58054". Lu AE58054 is a 5-HT$_6$ receptor antagonist and its chemical structure is depicted below:

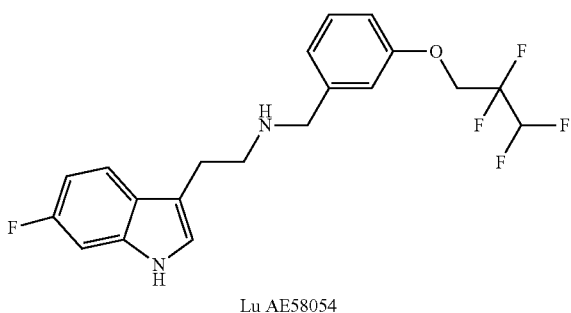 [SMILES: Fc1ccc2c(CCNCc3cccc(OCC(F)(F)C(F)F)c3)c[nH]c2c1]

Lu AE58054

Polymorphic form III of N-[2-(6-fluoro-1H-indol-3-yl)ethyl]-3-(2,2,3,3-tetrafluoropropoxy)benzylamine hydrochloride is characterized by an X-Ray powder diffractogram (XRPD) showing peaks at the following 2θ-angles: 4.63°, 6.94°, 13.89°, 17.26° and 19.97°, more specifically at the following 2θ-angles: 4.63°, 6.94°, 13.89°, 17.26°, 18.95°, 19.97°, 22.53° and 23.65° and even more specifically at the following 2θ-angles: 4.63°, 6.94°, 13.89°, 17.26°, 18.07°, 18.49°, 18.95°, 19.47°, 19.97°, 20.53°, 21.83°, 22.53°, 23.27°, 23.65° and 28.91°.

Polymorphic form I of N-[2-(6-fluoro-1H-indol-3-yl)ethyl]-3-(2,2,3,3-tetrafluoropropoxy)benzylamine hydrochloride is characterized by an X-Ray powder diffractogram showing peaks at the following 2θ-angles: 4.62°, 6.95°, 13.90°, 17.40°, 20.15° and 24.97°.

Polymorphic form II of N-[2-(6-fluoro-1H-indol-3-yl)ethyl]-3-(2,2,3,3-tetrafluoropropoxy)benzylamine hydrochloride is characterized by an X-Ray powder diffractogram showing peaks at the following 2θ-angles: 4.29°, 8.56°, 12.84°, 15.34°, 17.92° and 28.75°.

All XRPD data given herein are indicated as ±0.10 (°2θ).

The solids of N-[2-(6-fluoro-1H-indol-3-yl)ethyl]-3-(2,2,3,3-tetrafluoropropoxy)benzylamine hydrochloride obtained by the methods in the '488 patent and in WO 11/76212 are polymorphic form I and form II.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "a therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspects of the invention. The patient to be treated is preferably a mammal, in particular a human being.

Typically, the treatment of the present invention will involve daily administration of the compounds of the present invention. This may involve once daily administration, or administration twice a day or even more frequently.

A "therapeutically effective dose" of polymorphic form III of N-[2-(6-fluoro-1H-indol-3-yl)ethyl]-3-(2,2,3,3-tetrafluoropropoxy)benzylamine hydrochloride is an amount sufficient to provide an observable therapeutic benefit compared to baseline clinically observable signs and symptoms of Alzheimer's disease as measured by ADAS-cog, and Alzheimer's disease-related dementia treated in connection with the combination therapy.

"Immediate-release" is meant to include a conventional release, in which release of the drug starts immediately after administration. As used herein, the term "immediate release"

includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the anti-dementia drug within approximately 30 minutes after commencement of dissolution in a dissolution test.

The term "acetylcholinesterase inhibitor" is known to those skilled in art and includes compounds selected from the group consisting of donepezil, rivastigmine, galantamine and tacrine. The FDA approved dosages of the acetylcholinesterase inhibitor are encompassed by the instant invention. For example, the methods cover the dosages of donepezil shown to be effective in controlled clinical trials of the treatment of mild to moderate Alzheimer's disease are 5 mg or 10 mg administered orally once per day. A 23 mg orally once daily dose of donepezil is also approved for treating moderate to severe Alzheimer's disease.

The term "daily" means a given, continuous twenty-four (24) hour period.

The term "dose" is used herein to mean administration of polymorphic form III of the N-[2-(6-fluoro-1H-indol-3-yl)ethyl]-3-(2,2,3,3-tetrafluoropropoxy)benzylamine hydrochloride in one dosage form to the patient being treated. In some embodiments, the dose is a single oral formulation. In some embodiments, the dose is formulated as a tablet, a capsule, a pill, or a patch administered to the patient The term "effective daily dose" means the total amount of polymorphic form III of the N-[2-(6-fluoro-1H-indol-3-yl)ethyl]-3-(2,2,3,3-tetrafluoropropoxy)benzylamine hydrochloride administered to a patient in need of therapy in a continuous, twenty-four (24) hour period. As a non-limiting example used herein solely to illustrate the meaning of the term, an effective daily dose of 90 mg shall mean and include administering a single dose of 90 mg in a twenty four hour period, administering two doses of 45 mg each within a twenty four hour period, and administering three doses of 30 mg each in a twenty four hour period, and so on. When administering polymorphic form III of the N-[2-(6-fluoro-1H-indol-3-yl)ethyl]-3-(2,2,3,3-tetrafluoropropoxy)benzylamine hydrochloride in such a manner, i.e. more than once in a twenty four hour period, such administrations can be spread evenly through the twenty four hour period or even be administered simultaneously or nearly so.

The term "dose range" as used herein refers to an upper and a lower limit of an acceptable variation of the amount of agent specified. Typically, a dose of the agent in any amount within the specified range can be administered to patients undergoing treatment.

Pharmaceutical Compositions

In one embodiment, the present invention relates to pharmaceutical composition comprising polymorphic form III of N-[2-(6-fluoro-1H-indol-3-yl)ethyl]-3-(2,2,3,3-tetrafluoropropoxy)benzylamine hydrochloride.

In a further embodiment, the present invention relates to pharmaceutical formulation comprising polymorphic form III of the N-[2-(6-fluoro-1H-indol-3-yl)ethyl]-3-(2,2,3,3-tetrafluoropropoxy)benzylamine hydrochloride and pharmaceutically acceptable carriers or diluents The present invention further provides a pharmaceutical composition comprising a therapeutically effective amount of polymorphic form III of the N-[2-(6-fluoro-1H-indol-3-yl)ethyl]-3-(2,2,3,3-tetrafluoropropoxy)benzylamine hydrochlorideand optionally a pharmaceutically acceptable carrier or diluent. Polymorphic form III of the N-[2-(6-fluoro-1H-indol-3-yl)ethyl]-3-(2,2,3,3-tetrafluoropropoxy)benzylamine hydrochloride may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $22^{nd}$ Edition, Gennaro, Ed., Mack Publishing Co., Easton, Pa., 2013.

Suitable pharmaceutical carriers include inert solid diluents or fillers, sterile aqueous solution and various organic solvents. Examples of solid carriers are lactose, terra alba, sucrose, cyclodextrin, talc, agar, pectin, acacia, stearic acid and lower alkyl ethers of cellulose corn starch, potato starch, talcum, magnesium stearate, gelatine, lactose, gums, and the like. Other adjuvants or additives usually used for such purposes such as colourings, flavourings, preservatives etc. may be used provided that they are compatible with the active ingredients.

The pharmaceutical compositions formed by combining polymorphic form III of the N-[2-(6-fluoro-1H-indol-3-yl)ethyl]-3-(2,2,3,3-tetrafluoropropoxy)benzylamine hydrochloride and the pharmaceutical acceptable carriers are then readily administered in a variety of dosage forms suitable for the disclosed routes of administration. The formulations may be presented in dosage form by methods known in the art of pharmacy.

Formulations of the present invention suitable for oral administration may be presented as discrete units such as capsules or tablets, each containing a predetermined amount of the active ingredient, and which may include one or more suitable excipients. The orally available formulations may be in the form of a powder or granules, a solution or suspension in an aqueous or non-aqueous liquid, or an oil-in-water or water-in-oil liquid emulsion. If a solid carrier is used for oral administration, the preparation may be tabletted, placed in a hard gelatine capsule in powder or pellet form or it can be in the form of a troche or lozenge.

Without limiting the scope of the invention, an example of an immediate release formulation of a once daily 30 mg dose of polymorphic form III of the N-[2-(6-fluoro-1H-indol-3-yl)ethyl]-3-(2,2,3,3-tetrafluoropropoxy)benzylamine hydrochloride is the following:

| | |
|---|---|
| Polymorphic form III of N-[2-(6-fluoro-1H-indol-3-yl)ethyl]-3-(2,2,3,3-tetrafluoropropoxy)benzylamine hydrochloride | 32.75 mg |
| Calcium Phosphohate Dibasic | 222.0 mg |
| Colloidal Sllicon Dioxide NF (Aerosil 200) | 3.900 mg |
| Magnesium Sterate NF (Vegatable Grade) | 1.300 mg |

The formulation can be encapsulated e.g. in a Gelatin Capsule Size #3.

In a similar manner, pharmaceutical compositions may be prepared comprising the administration of polymorphic form III of the N-[2-(6-fluoro-1H-indol-3-yl)ethyl]-3-(2,2,3,3-tetrafluoropropoxy)benzylamine hydrochloride wherein the dose ranges administered are between about 5 mg and about 120 mg.

Methods of Treatment

Provided herein is a combination therapy useful for the treatment of mild, moderate and severe Alzheimer's disease, as well as symptoms associated with mild to moderate Alzheimer's disease. As discussed below, the methods provided herein have a number of advantages.

The term "Alzheimer's disease" refers to a progressive disease of the human central nervous system. It is manifested by dementia typically in the elderly, by disorientation, loss of memory, difficulty with language, calculation, or visual-spatial skills, and by psychiatric manifestations. It is associated with degenerating neurons in several regions of the brain. The term "dementia" as used herein includes, but is not restricted to, Alzheimer's dementia with or without psychotic symptoms.

In a particular embodiment, the therapeutic methods provided herein are effective for the treatment of mild, moderate and severe Alzheimer's disease in a subject. Phases of Alzheimer's further include "moderately severe cognitive decline," also referred to as "moderate or mid-stage Alzheimer's disease;" "severe cognitive decline," also referred to as "moderately severe or mid-stage Alzheimer's disease;" and "very severe cognitive decline," also referred to as "severe or late-stage Alzheimer's disease." Moderately severe cognitive decline is characterized by major gaps in memory and deficits in cognitive function emerge. At this stage, some assistance with day-to-day activities becomes essential. In severe cognitive decline, memory difficulties continue to worsen, significant personality changes may emerge and affected individuals need extensive help with customary daily activities. Late stage Alzheimer's disease or very severe cognitive decline is the final stage of the disease when individuals lose the ability to respond to their environment, the ability to speak and, ultimately, the ability to control movement.

In another embodiment, the patient to be treated by the combination therapy of the invention has an MMSE score between 12 and 22. "MMSE" refers to the Mini-Mental State Examination used in the cognitive assessment community.

In one embodiment, the present invention relates to a method of treating Alzheimer's disease as adjunctive therapy to acetylcholinesterase treatment comprising administering an effective daily dose of polymorphic form III of N-[2-(6-fluoro-1H-indol-3-yl)ethyl]-3-(2,2,3,3-tetrafluoropropoxy)benzylamine hydrochloride a patient in need of such treatment. In a further embodiment, the effective daily dose administered to the patient of polymorphic form III of N-[2-(6-fluoro-1H-indol-3-yl)ethyl]-3-(2,2,3,3-tetrafluoropropoxy)benzylamine hydrochloride is between about 5 and about 120 mg. In a further embodiment, the effective daily dose administered to the patient of polymorphic form III of N-[2-(6-fluoro-1H-indol-3-yl)ethyl]-3-(2,2,3,3-tetrafluoropropoxy)benzylamine hydrochloride is between about 30 and about 60 mg. In a further embodiment, the acetylcholinesterase inhibitor is donepezil. In a further embodiment, the acetylcholinesterase inhibitor is rivastigmine. In a further embodiment, the acetylcholinesterase inhibitor is galantamine. In a further embodiment, the acetylcholinesterase inhibitor is tacrine.

In one embodiment, the present invention relates to a method of treating a disease or disorder selected from dementia in Parkinson's disease, Huntington's chorea and Down's syndrome comprising administering an effective daily dose of polymorphic form III of N-[2-(6-fluoro-1H-indol-3-yl)ethyl]-3-(2,2,3,3-tetrafluoropropoxy)benzylamine hydrochloride to a patient in need of such treatment.

In one embodiment, the present invention relates to a method of treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis comprising administering an effective daily dose of polymorphic form III of N-[2-(6-fluoro-1H-indol-3-yl)ethyl]-3-(2,2,3,3-tetrafluoropropoxy)benzylamine hydrochloride to a patient in need of such treatment In one embodiment, the present invention relates to polymorphic form III of N-[2-(6-fluoro-1H-indol-3-yl)ethyl]-3-(2,2,3,3-tetrafluoropropoxy)benzylamine hydrochloride for use in treating Alzheimer's disease as adjunctive therapy to acetylcholinesterase treatment. In a further embodiment, the dose of polymorphic form III of N-[2-(6-fluoro-1H-indol-3-yl)ethyl]-3-(2,2,3,3-tetrafluoropropoxy)benzylamine hydrochloride is between about 5 and about 120 mg. In a further embodiment, the dose of polymorphic form III of N-[2-(6-fluoro-1H-indol-3-yl)ethyl]-3-(2,2,3,3-tetrafluoropropoxy)benzylamine hydrochloride is between about 30 and about 60 mg. In a further embodiment, the acetylcholinesterase inhibitor is donepezil. In a further embodiment, the acetylcholinesterase inhibitor is rivastigmine. In a further embodiment, the acetylcholinesterase inhibitor is galantamine. In a further embodiment, the acetylcholinesterase inhibitor is tacrine.

In one embodiment, the present invention relates to polymorphic form III of N-[2-(6-fluoro-1H-indol-3-yl)ethyl]-3-(2,2,3,3-tetrafluoropropoxy)benzylamine hydrochloride for use in treating a disease or disorder selected from dementia in Parkinson's disease, Huntington's chorea and Down's syndrome.

In one embodiment, the present invention relates to polymorphic form III of N-[2-(6-fluoro-1H-indol-3-yl)ethyl]-3-(2,2,3,3-tetrafluoropropoxy)benzylamine hydrochloride for use in treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis.

In one embodiment, the present invention relates to use of polymorphic form III of N-[2-(6-fluoro-1H-indol-3-yl)ethyl]-3-(2,2,3,3-tetrafluoropropoxy)benzylamine hydrochloride for the manufacture of a medicament for treating Alzheimer's disease as adjunctive therapy to acetylcholinesterase treatment. In a further embodiment, the dose of polymorphic form III of N-[2-(6-fluoro-1H-indol-3-yl)ethyl]-3-(2,2,3,3-tetrafluoropropoxy)benzylamine hydrochloride is between about 5 and about 120 mg. In a further embodiment, the dose of polymorphic form III of N-[2-(6-fluoro-1H-indol-3-yl)ethyl]-3-(2,2,3,3-tetrafluoropropoxy)benzylamine hydrochloride is between about 30 and about 60 mg. In a further embodiment, the acetylcholinesterase inhibitor is donepezil. In a further embodiment, the acetylcholinesterase inhibitor is rivastigmine. In a further embodiment, the acetylcholinesterase inhibitor is galantamine. In a further embodiment, the acetylcholinesterase inhibitor is tacrine.

In one embodiment, the present invention relates to use of polymorphic form III of N-[2-(6-fluoro-1H-indol-3-yl)ethyl]-3-(2,2,3,3-tetrafluoropropoxy)benzylamine hydrochloride for the manufacture of a medicament for treating a disease or disorder selected from dementia in Parkinson's disease, Huntington's chorea and Down's syndrome.

In one embodiment, the present invention relates to use of polymorphic form III of N-[2-(6-fluoro-1H-indol-3-yl)ethyl]-3-(2,2,3,3-tetrafluoropropoxy)benzylamine hydrochloride for the manufacture of a medicament for treating a disease or disorder selected from cognitive disorders, age-related cognitive disorder, mild cognitive impairment, mood disorders (including depression, mania, bipolar disorders), psychosis (in particular schizophrenia), anxiety, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified (particularly including generalized anxiety disorder, panic disorder, and obsessive compulsive disorder), idiopathic and drug-induced Parkinson's disease, epilepsy, convulsions, migraine (including migraine headache), substance withdrawal (including, substances such as opiates, nicotine, tobacco products, alcohol, benzodiazepines, cocaine, sedatives, hypnotics, etc.), sleep disorders (including narcolepsy), attention deficit/hyperactivity disorder, conduct disorder, learning disorders, dementia (including Alzheimer's disease and AIDS-induced dementia), Huntington's Chorea, cognitive deficits subsequent to cardiac bypass surgery and grafting, stroke, cerebral ischemia, spinal cord trauma, head trauma, perinatal hypoxia, cardiac arrest, hypoglycemic neuronal damage, vascular dementia, multi-infarct dementia, amylotrophic lateral sclerosis, and multiple sclerosis.

EXPERIMENTAL SECTION

X-Ray Powder Diffractograms (XRPD)

X-Ray powder diffractograms (XRPD) were measured on a PANalytical X'Pert PRO X-Ray Diffractometer using CuKαi radiation. The samples were measured in reflection mode in the 2θ-range 3-40° using an X'celerator detector. Diffraction data are indicated ±0.10 (°2θ).

IR Spectra Obtained by Fourier Transform Infrared Spectroscopy (FTIR)

The infrared spectra (IR spectra) are recorded on a TENSOR 27 FTIR spectrometer from BRUKER equipped with an attenuated total reflectance (ATR) unit with a diamond single reflecting element.

The spectra are obtained using a spectral resolution of 1 $cm^{-1}$ and 32 scan. IR bands given are indicated as ±1 $cm^{-1}$.

Example 1

Synthesis of N-[2-(6-fluoro-1H-indol-3-yl)ethyl]-3-(2,2,3,3-tetrafluoropropoxy)benzylamine hydrochloride The synthesis of N-[2-(6-fluoro-1H-indol-3-yl)ethyl]-3-(2,2,3,3-tetrafluoropropoxy)benzylamine hydrochloride can be found in U.S. Pat. No. 7,157,488, which is hereby incorporated by reference in its entirety. See e.g. column 109, line 1 through column 110, line 3 for a synthesis starting with commercially available 6-fluoroindole.

Example 2

Preparation of polymorphic form III of N-[2-(6-fluoro-1H-indol-3-yl)ethyl]-3-(2,2,3,3-tetrafluoropropoxy)benzylamine hydrochloride 6 mL of a solvent or solvent mixture is added into a glass vial together with polymorphic form I of N-[2-(6-fluoro-1H-indol-3-yl)ethyl]-3-(2,2,3,3-tetrafluoropropoxy)benzylamine hydrochloride. The added amount of compound is determined by the expected solubility in the relevant solvent or solvent system. If a clear solution is obtained anti-solvent and/or additional polymorphic form I of N-[2-(6-fluoro-1H-indol-3-yl)ethyl]-3-(2,2,3,3-tetrafluoropropoxy)benzylamine hydrochlorideis added until it is a suspension at the relevant temperature. The suspension is slurred for a prolonged period of time. The result of the slurry experiment is evaluated by filtering off the solid material and measuring XRPD on the isolated solid.

Slurry in a toluene/acetonitrile solvent mixture at 50° C.:

6 mL of a toluene/acetonitrile (4:1) solvent mixture was added into a glass vial and 100 mg polymorphic form I of N-[2-(6-fluoro-1H-indol-3-yl)ethyl]-3-(2,2,3,3-tetrafluoropropoxy)benzylamine hydrochloride was added. The resulting suspension was heated to 50° C. A clear solution was obtained and another 50 mg was added. The suspension was stirred for one month at 50° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in an acetone/heptane solvent mixture at 50° C.:

6 mL of an acetone/heptane (1:4) solvent mixture was added into a glass vial and 100 mg polymorphic form I of N-[2-(6-fluoro-1H-indol-3-yl)ethyl]-3-(2,2,3,3-tetrafluoropropoxy)benzylamine hydrochloride was added. The resulting suspension was heated to 50° C. The suspension was stirred for one week at 50° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in a methanol/toluene solvent mixture at 50° C.:

6 mL of a methanol/toluene (1:9) solvent mixture was added into a glass vial and 100 mg polymorphic form I of N-[2-(6-fluoro-1H-indol-3-yl)ethyl]-3-(2,2,3,3-tetrafluoropropoxy)benzylamine hydrochloride was added. After stirring another 1 mL of the anti-solvent (toluene) was added +50 mg polymorphic form I of N-[2-(6-fluoro-1H-indol-3-yl)ethyl]-3-(2,2,3,3-tetrafluoropropoxy)benzylamine hydrochloride. Stirring resulted in a clear solution and 1 mL of toluene was added and additional 50 mg polymorphic form I of N-[2-(6-fluoro-1H-indol-3-yl)ethyl]-3-(2,2,3,3-tetrafluoropropoxy)benzylamine hydrochloride. Stirring still resulted in a clear solution and the total volume of 8 mL was divided into two. To the 4 mL solutions another 1 mL of toluene was added and additional 50 mg polymorphic form I of N-[2-(6-fluoro-1H-indol-3-yl)ethyl]-3-(2,2,3,3-tetrafluoropropoxy)benzylamine hydrochloride. The resulting suspension was heated to 50° C. A clear solution was obtained and substance was added until a suspension was obtained. The suspension was stirred for one week at 50° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in isopropyl acetate at 50° C.:

6 mL of isopropyl acetate was added into a glass vial and 50 mg polymorphic form I of N-[2-(6-fluoro-1H-indol-3-yl)ethyl]-3-(2,2,3,3-tetrafluoropropoxy)benzylamine hydrochloride was added. The resulting suspension was heated to 50° C. A clear solution was obtained and another 50 mg polymorphic form I of N-[2-(6-fluoro-1H-indol-3-yl)ethyl]-3-(2,2,3,3-tetrafluoropropoxy)benzylamine hydrochloride was added. Substance was added until a suspension was obtained at 50° C. The suspension was stirred for one week at 50° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in ethyl acetate at 50° C.:

6 mL of ethyl acetate was added into a glass vial and 150 mg polymorphic form I of N-[2-(6-fluoro-1H-indol-3-yl)ethyl]-3-(2,2,3,3-tetrafluoropropoxy)benzylamine hydrochloride was added. The resulting suspension was heated to 50° C. on a thermal stirrer plate. A clear solution was obtained and 50 mg polymorphic form I of N-[2-(6-fluoro-1H-indol-3-yl)ethyl]-3-(2,2,3,3-tetrafluoropropoxy)benzylamine hydrochloride was added. Polymorphic form I of N-[2-(6-fluoro-1H-indol-3-yl)ethyl]-3-(2,2,3,3-tetrafluoropropoxy)benzylamine hydrochloride was added until a suspension was obtained. The suspension was stirred for one month at 50° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Polymorphic form I of N-[2-(6-fluoro-1H-indol-3-yl)ethyl]-3-(2,2,3,3-tetrafluoropropoxy)benzylamine hydrochloride is transformed into polymorphic form III of N-[2-(6-fluoro-1H-indol-3-yl)ethyl]-3-(2,2,3,3-tetrafluoropropoxy)benzylamine hydrochloride when slurred at 50° C. As no solvate is formed, this shows that polymorphic form III of N-[2-(6-fluoro-1H-indol-3-yl)ethyl]-3-(2,2,3,3-tetrafluoropropoxy)benzylamine hydrochloride is less soluble and therefore thermodynamically stable at 50° C.

Slurry in isopropyl acetate at 25° C.:

6 mL of isopropyl acetate was added into a glass vial and 50 mg polymorphic form I of N-[2-(6-fluoro-1H-indol-3-yl)ethyl]-3-(2,2,3,3-tetrafluoropropoxy)benzylamine hydrochloride was added. The suspension was stirred for one month at 25° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in dichloromethane at 25° C.:

6 mL of dichloromethane was added into a glass vial and 50 mg polymorphic form I of N-[2-(6-fluoro-1H-indol-3-yl)ethyl]-3-(2,2,3,3-tetrafluoropropoxy)benzylamine hydrochloride was added. The suspension was stirred for one month at 25° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Slurry in 2-butanol at 25° C.:

6 mL of 2-butanol was added into a glass vial and 100 mg polymorphic form I of N-[2-(6-fluoro-1H-indol-3-yl)ethyl]-3-(2,2,3,3-tetrafluoropropoxy)benzylamine hydrochloride was added. The suspension was stirred for one month at 25° C. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Polymorphic form I of N-[2-(6-fluoro-1H-indol-3-yl)ethyl]-3-(2,2,3,3-tetrafluoropropoxy)benzylamine hydrochloride is transformed into polymorphic form III of N-[2-(6-fluoro-1H-indol-3-yl)ethyl]-3-(2,2,3,3-tetrafluoropropoxy)benzylamine hydrochloride when slurred at 25° C. As no solvate is formed, this shows that polymorphic form III of N-[2-(6-fluoro-1H-indol-3-yl)ethyl]-3-(2,2,3,3-tetrafluoropropoxy)benzylamine hydrochloride is less soluble and therefore thermodynamically stable at 25° C.

Slurry in a methanol/toluene solvent mixture at 5° C.:

6 mL of a methanol/toluene (1:9) solvent mixture was added into a glass vial and 100 mg polymorphic form I of N-[2-(6-fluoro-1H-indol-3-yl)ethyl]-3-(2,2,3,3-tetrafluoropropoxy)benzylamine hydrochloride was added. After stirring another 1 mL of the anti-solvent (toluene) was added+ 50 mg polymorphic form I of N-[2-(6-fluoro-1H-indol-3-yl)ethyl]-3-(2,2,3,3-tetrafluoropropoxy)benzylamine hydrochloride. Stirring resulted in a clear solution and 1 mL of toluene was added and additional 50 mg polymorphic form I of N-[2-(6-fluoro-1H-indol-3-yl)ethyl]-3-(2,2,3,3-tetrafluoropropoxy)benzylamine hydrochloride. Stirring still resulted in a clear solution and the total volume of 8 mL was divided into two. To the 4 mL solutions another 1 mL of toluene was added and additional 50 mg polymorphic form I of N-[2-(6-fluoro-1H-indol-3-yl)ethyl]-3-(2,2,3,3-tetrafluoropropoxy)benzylamine hydrochloride. The saturated supernatant together with a small amount of solid from the obtained suspension was transferred to a glass vial and stirred in the refrigerator at 5° C. for three month. Polymorphic form III of N-[2-(6-fluoro-1H-indol-3-yl)ethyl]-3-(2,2,3,3-tetrafluoropropoxy)benzylamine hydrochloride was obtained as evaluated by XRPD.

Polymorphic form I of N-[2-(6-fluoro-1H-indol-3-yl)ethyl]-3-(2,2,3,3-tetrafluoropropoxy)benzylamine hydrochloride is transformed into polymorphic form III of N-[2-(6-fluoro-1H-indol-3-yl)ethyl]-3-(2,2,3,3-tetrafluoropropoxy)benzylamine hydrochloride when slurred at 5° C. As no solvate is formed, this shows that polymorphic form III of N-[2-(6-fluoro-1H-indol-3-yl)ethyl]-3-(2,2,3,3-tetrafluoropropoxy)benzylamine hydrochloride is less soluble and therefore thermodynamically stable at 5° C.

Example 3

Preparation of Polymorphic Form III of N-[2-(6-fluoro-1H-indol-3-yl)ethyl]-3-(2,2,3,3-tetrafluoropropoxy)benzylamine hydrochloride by Seeding Polymorphic form I of N-[2-(6-fluoro-1H-indol-3-yl)ethyl]-3-(2,2,3,3-tetrafluoropropoxy)benzylamine hydrochloride(3858 g) in a mixture of acetonitrile (4.55 kg) and toluene (5 kg) was warmed to 80° C. to obtain a clear solution. The solution was then cooled to 45° C. before seeding with polymorphic form III of N-[2-(6-fluoro-1H-indol-3-yl)ethyl]-3-(2,2,3,3-tetrafluoropropoxy)benzylamine hydrochloride(4.8 g) and then cooled further to 42° C. After 18 hours a portion of toluene (7.2 kg) was added, followed by additional toluene portion (16.7 kg) and stirred at approximately. 45° C. for 3 days, cooled and filtered to give polymorphic form III of N-[2-(6-fluoro-1H-indol-3-yl)ethyl]-3-(2,2,3,3-tetrafluoropropoxy)benzylamine hydrochloride which was washed with toluene (3.9 kg). The compound was dried to give polymorphic form III of N-[2-(6-fluoro-1H-indol-3-yl)ethyl]-3-(2,2,3,3-tetrafluoropropoxy)benzylamine hydrochloride (3.722 kg).

Polymorphic form I of N-[2-(6-fluoro-1H-indol-3-yl)ethyl]-3-(2,2,3,3-tetrafluoropropoxy)benzylamine hydrochloride (40 g) in toluene (480 mL) under an atmosphere of nitrogen was heated to 110° C. before cooling slowly down to 52° C. The suspension was then seeded with polymorphic form III of N-[2-(6-fluoro-1H-indol-3-yl)ethyl]-3-(2,2,3,3-tetrafluoropropoxy)benzylamine hydrochloride and stirred overnight. A small sample of the suspension was taken cooled and filtered; the solid obtained was analyzed by XRPD to be polymorphic form II of N-[2-(6-fluoro-1H-indol-3-yl)ethyl]-3-(2,2,3,3-tetrafluoropropoxy)benzylamine hydrochloride. The temperature of the suspension was lowered to 45° C. before seeding with polymorphic form III of N-[2-(6-fluoro-1H-indol-3-yl)ethyl]-3-(2,2,3,3-tetrafluoropropoxy)benzylamine hydrochloride and stirred overnight. A small sample of the suspension was taken cooled and filtered; the solid obtained was analyzed by XRPD to be polymorphic form II of N-[2-(6-fluoro-1H-indol-3-yl)ethyl]-3-(2,2,3,3-tetrafluoropropoxy)benzylamine hydrochloride. The suspension at 45° C. was seeded with polymorphic form III of N-[2-(6-fluoro-1H-indol-3-yl)ethyl]-3-(2,2,3,3-tetrafluoropropoxy)benzylamine hydrochloride and stirred for two days. A small sample of the suspension was taken cooled and filtered; the solid obtained was analyzed by XRPD to be a mixture of polymorphic form II and III of N-[2-(6-fluoro-1H-indol-3-yl)ethyl]-3-(2,2,3,3-tetrafluoropropoxy)benzylamine hydrochloride. The temperature of the suspension was lowered to 40° C. before seeding with polymorphic form III of N-[2-(6-fluoro-1H-indol-3-yl)ethyl]-3-(2,2,3,3-tetrafluoropropoxy)benzylamine hydrochloride and stirred overnight. A small sample of the suspension was taken cooled and filtered; the solid obtained was analyzed by XRPD to be a mixture of polymorphic form II and III of N-[2-(6-fluoro-1H-indol-3-yl)ethyl]-3-(2,2,3,3-tetrafluoropropoxy)benzylamine hydrochloride. Acetonitrile (50 mL) was added before seeding with polymorphic form III of N-[2-(6-fluoro-1H-indol-3-yl)ethyl]-3-(2,2,3,3-tetrafluoropropoxy)benzylamine hydrochloride and stirred overnight at 40° C. A small sample of the suspension was taken cooled and filtered; the solid obtained was analyzed by XRPD to polymorphic form III of N-[2-(6-fluoro-1H-indol-3-yl)ethyl]-3-(2,2,3,3-tetrafluoropropoxy)benzylamine hydrochloride with traces of polymorphic form I.

Polymorphic form I of N-[2-(6-fluoro-1H-indol-3-yl)ethyl]-3-(2,2,3,3-tetrafluoropropoxy)benzylamine hydrochloride (40 g) in isopropyl acetate (480 mL) under an atmosphere of nitrogen was heated to 81° C. to give a clear solution before cooling slowly down to 50° C. then seeded with polymorphic form III of N-[2-(6-fluoro-1H-indol-3-yl)ethyl]-3-(2,2,3,3-tetrafluoropropoxy)benzylamine hydrochloride and stirred overnight. A small sample of the suspension was taken cooled and filtered; the solid obtained was analyzed by XRPD to be polymorphic form II of N-[2-(6-fluoro-1H-indol-3-yl)ethyl]-3-(2,2,3,3-tetrafluoropropoxy)benzylamine hydrochloride with traces of polymorphic form I or III. The temperature of the suspension was lowered to 45° C. before seeding with polymorphic form III of N-[2-(6-fluoro-1H-indol-3-yl)ethyl]-3-(2,2,3,3-tetrafluoropropoxy)benzylamine hydrochloride and stirred overnight. A small sample of the suspension was taken cooled and filtered; the solid obtained was analyzed by XRPD to be polymorphic form II of N-[2-(6-fluoro-1H-indol-3-yl)ethyl]-3-(2,2,3,3-tetrafluoropropoxy)benzylamine hydrochloride with traces of polymorphic form I or III. The suspension at 45° C. was seeded with polymorphic form III of N-[2-(6-fluoro-1H-indol-3-yl)ethyl]-3-(2,2,3,3-tetrafluoropropoxy)benzylamine hydrochloride and stirred for three days. A small sample of the suspension was taken cooled and filtered; the solid obtained was analyzed by XRPD to be to be polymorphic form II of N-[2-(6-fluoro-1H-indol-3-yl)ethyl]-3-(2,2,3,3-tetrafluoropropoxy)benzylamine hydrochloride with traces of polymorphic form I/III. The suspension at 45° C. was seeded with polymorphic form III of N-[2-(6-fluoro-1H-indol-3-yl)ethyl]-3-(2,2,3,3-tetrafluoropropoxy)benzylamine hydrochloride and stirred for six days. A small sample of the suspension was taken cooled and filtered; the solid obtained was analyzed by XRPD to be polymorphic form III of N-[2-(6-fluoro-1H-indol-3-yl)ethyl]-3-(2,2,3,3-tetrafluoropropoxy)benzylamine hydrochloride. The solution was cooled to 5° C. and isolated by filtration, dried under reduced pressure to give polymorphic form III of N-[2-(6-fluoro-1H-indol-3-yl)ethyl]-3-(2,2,3,3-tetrafluoropropoxy)benzylamine hydrochloride (37.6 g).

Heating polymorphic form I of N-[2-(6-fluoro-1H-indol-3-yl)ethyl]-3-(2,2,3,3-tetrafluoropropoxy)benzylamine hydrochloride in toluene as describe above will result in the formation of polymorphic form II upon cooling from 110° C. as polymorphic form II is the most stable at temperatures above 60° C., and more easily formed than the polymorphic form III. Lowering the temperature and adding acetonitrile to the slurry and thereby getting a higher solubility, resulted in polymorphic form III. The traces of polymorphic form I could be obtained when evaporating the solvent during filtration indicating that polymorphic form I is more easily formed compared to polymorphic form III at lower temperatures.

Polymorphic form I of N-[2-(6-fluoro-1H-indol-3-yl)ethyl]-3-(2,2,3,3-tetrafluoropropoxy)benzylamine hydrochloride(49 g), in a mixture of acetonitrile (74 mL) and toluene (74 mL) was warmed to 84° C. to obtain a clear solution under a nitrogen atmosphere. The solution was slowly cooled to 45° C. over approximately 1 hour before seeding with polymorphic form III of N-[2-(6-fluoro-1H-indol-3-yl)ethyl]-3-(2,2,3,3-tetrafluoropropoxy)benzylamine hydrochloride (100 mg) and stirred between 41-43° C. for approximately 1.5 hours. Toluene (200 mL) was slowly added maintaining the temperature between 40-43° C. The suspension was then warmed slowly to 50° C. and stirred at this temperature for 17 hours. The suspension was then slowly cooled to 31° C. and filtered and washed with a mixture of toluene (162 mL) and acetonitrile (18 mL). The compound was dried to give polymorphic form III of N-[2-(6-fluoro-1H-indol-3-yl)ethyl]-3-(2,2,3,3-tetrafluoropropoxy)benzylamine hydrochloride (44.8 g).

Example 4

Evaporation Crystallization Experiments 4.5 mL ethyl acetate and 45 mg of polymorphic form I of N-[2-(6-fluoro-1H-indol-3-yl)ethyl]-3-(2,2,3,3-tetrafluoropropoxy)benzylamine hydrochloride was added to a glass vial and stirred for a few minutes to obtain a clear solution. The solution was divided in three.

A ⅓ of the solution was kept at 25° C., without cap, for more rapid evaporation resulting in polymorphic form I of N-[2-(6-fluoro-1H-indol-3-yl)ethyl]-3-(2,2,3,3-tetrafluoropropoxy)benzylamine hydrochloride.

A ⅓ of the solution was kept at 50° C., without cap, for more rapid evaporation resulting in polymorphic form II of N-[2-(6-fluoro-1H-indol-3-yl)ethyl]-3-(2,2,3,3-tetrafluoropropoxy)benzylamine hydrochloride.

A ⅓ of the solution was kept at 50° C., with a cap with a pinhole, for slow evaporation resulting in polymorphic form II of N-[2-(6-fluoro-1H-indol-3-yl)ethyl]-3-(2,2,3,3-tetrafluoropropoxy)benzylamine hydrochloride.

3 mL of a 2 butanone/heptane (1:4) solvent mixture and 45 mg of polymorphic form I of N-[2-(6-fluoro-1H-indol-3-yl)ethyl]-3-(2,2,3,3-tetrafluoropropoxy)benzylamine hydrochloride was added to a glass vial and stirred for a few minutes resulting in a suspension. 1 mL of 2-butanone was added but solid material was still observed. 1 mL of the solution was removed and 1 mL of 2-butanone was added and a clear solution was obtained. The solution was divided in three.

A ⅓ of the solution was kept at 25° C., without cap, for more rapid evaporation resulting in polymorphic form I of N-[2-(6-fluoro-1H-indol-3-yl)ethyl]-3-(2,2,3,3-tetrafluoropropoxy)benzylamine hydrochloride.

A ⅓ of the solution was kept at 50° C., without cap, for more rapid evaporation resulting in polymorphic form II of N-[2-(6-fluoro-1H-indol-3-yl)ethyl]-3-(2,2,3,3-tetrafluoropropoxy)benzylamine hydrochloride.

A ⅓ of the solution was kept at 50° C., with a cap with a pinhole, for slow evaporation resulting in polymorphic form I of N-[2-(6-fluoro-1H-indol-3-yl)ethyl]-3-(2,2,3,3-tetrafluoropropoxy)benzylamine hydrochloride.

Evaporation of the solvent from a solution of N-[2-(6-fluoro-1H-indol-3-yl)ethyl]-3-(2,2,3,3-tetrafluoropropoxy) benzylamine hydrochloride at 25° C. and 50° C. results in the formation of polymorphic form I and II and not form III. The results of these experiments indicate that polymorphic form I and form II of N-[2-(6-fluoro-1H-indol-3-yl)ethyl]-3-(2,2,3,3-tetrafluoropropoxy)benzylamine hydrochloride have a kinetic advantage over polymorphic form III which is the thermodynamically stable form at these temperatures.

Example 5

Relative Stability of Polymorphic Form I, II and III of N-[2-(6-fluoro-1H-indol-3-yl)ethyl]-3-(2,2,3,3-tetrafluoropropoxy)benzylamine hydrochloride A saturated solution was prepared by heating 1.6 mL isopropyl acetate and 0.4 mL heptane to 70° C. and adding 50 mg of polymorphic form I of N-[2-(6-fluoro-1H-indol-3-yl)ethyl]-3-(2,2,3,3-tetrafluoropropoxy)benzylamine hydrochloride. Stirring for two hours and then left non-stirred at 70° C. overnight resulted in a saturated solution where solid material could be seen.

The supernatant was divided into two ampoules and kept at 60° C. and 70° C.

5 mg of polymorphic form I, II and III of N-[2-(6-fluoro-1H-indol-3-yl)ethyl]-3-(2,2,3,3-tetrafluoropropoxy)benzylamine hydrochloride was added to the 60° C. solution and left stirring at 60° C. for one and four days, respectively. Evaluation after one day resulted in a mixture of polymorphic form II and III of N-[2-(6-fluoro-1H-indol-3-yl)ethyl]-3-(2,2,3,3-tetrafluoropropoxy)benzylamine hydrochloride and polymorphic form I has vanished. Evaluation after four days resulted in polymorphic form II of N-[2-(6-fluoro-1H-indol-3-yl)ethyl]-3-(2,2,3,3-tetrafluoropropoxy)benzylamine hydrochloride and traces of polymorphic form III.

2.5 mg of polymorphic form I, II and III of N-[2-(6-fluoro-1H-indol-3-yl)ethyl]-3-(2,2,3,3-tetrafluoropropoxy) benzylamine hydrochloride was added to the 70° C. solution and left without stirring at 70° C. for three days. Evaluation resulted in polymorphic form II and I of N-[2-(6-fluoro-1H-indol-3-yl)ethyl]-3-(2,2,3,3-tetrafluoropropoxy)benzylamine hydrochloride and polymorphic form III has vanished.

Polymorphic form I, II and III of N-[2-(6-fluoro-1H-indol-3-yl)ethyl]-3-(2,2,3,3-tetrafluoropropoxy)benzylamine hydrochloride were mixed in equal amounts and slurred in isopropyl acetate at 60° C. After one day it is only a mixture of polymorphic form II and III of N-[2-(6-fluoro-1H-indol-3-yl)ethyl]-3-(2,2,3,3-tetrafluoropropoxy)benzylamine hydrochloride while polymorphic form I has vanished. After four days it can be seen that polymorphic form III of the N-[2-(6-fluoro-1H-indol-3-yl)ethyl]-3-(2,2,3,3-tetrafluoropropoxy)benzylamine hydrochloride is transforming into polymorphic form II. This shows that polymorphic form I of N-[2-(6-fluoro-1H-indol-3-yl)ethyl]-3-(2,2,3,3-tetrafluoropropoxy)benzylamine hydrochloride is less stable than polymorphic form III and polymorphic form II is thermodynamically stable at this temperature. The fact that the transformation is slow indicates that it is close to the transition temperature between polymorphic form II and III of N-[2-(6-fluoro-1H-indol-3-yl)ethyl]-3-(2,2,3,3-tetrafluoropropoxy)benzylamine hydrochloride. At 70° C. the transformation is faster and a suspension of equal amounts of polymorphic form I, II and III of N-[2-(6-fluoro-1H-indol-3-yl)ethyl]-3-(2,2,3,3-tetrafluoropropoxy)benzylamine hydrochloride left without stirring will turn into polymorphic form II in three days. This shows that polymorphic form II of N-[2-(6-fluoro-1H-indol-3-yl)ethyl]-3-(2,2,3,3-tetrafluoropropoxy)benzylamine hydrochloride is thermodynamically stable at 70° C.

Example 6

Solubility in Organic Solvents

Thermodynamic solubility of polymorphic form I and III of N-[2-(6-fluoro-1H-indol-3-yl)ethyl]-3-(2,2,3,3-tetrafluoropropoxy)benzylamine hydrochloride was measured by shaking an excess amount of the two polymorphic forms in the organic solvent in a sealed container at room temperature (about 23° C.). After equilibrium was attained, a sample was withdrawn, the solid filtered or centrifuged off and the clear filtrate/supernatant was assayed by HPLC at 217 nm. The precipitate was evaluated by XRPD to determine the polymorphic form.

Table 2: Solubility of polymorphic form III and form I of N-[2-(6-fluoro-1H-indol-3-yl)ethyl]-3-(2,2,3,3-tetrafluoropropoxy)benzylamine hydrochloride in organic solvents.

TABLE 2

| Solvent | Solubility - polymorphic form III [mg base/mL] | Solubility - polymorphic form I [mg base/mL] |
|---|---|---|
| 2-butanol | 9.3 | 10.5 |
| Isopropanol | 24.5 | 25.2 |
| Isopropyl acetate | 3.0 | 3.4 |

Solubility experiments in organic solvents show that polymorphic form III of N-[2-(6-fluoro-1H-indol-3-yl)ethyl]-3-(2,2,3,3-tetrafluoropropoxy)benzylamine hydrochloride is slightly less soluble and therefore thermodynamically stable at room temperature (about 23° C.).

Example 7

Preparation of a Mixture of Polymorphic Form III and Polymorphic Form IV

A saturated solution of ethanol and polymorphic form III of N-[2-(6-fluoro-1H-indol-3-yl)ethyl]-3-(2,2,3,3-tetrafluoropropoxy)benzylamine hydrochloride is prepared at room temperature. The slurry is left to equilibrate under constant stirring. A small sample of the slurry containing both liquid and solid material is taken out with a pipette and left to evaporate.

Figure 7:
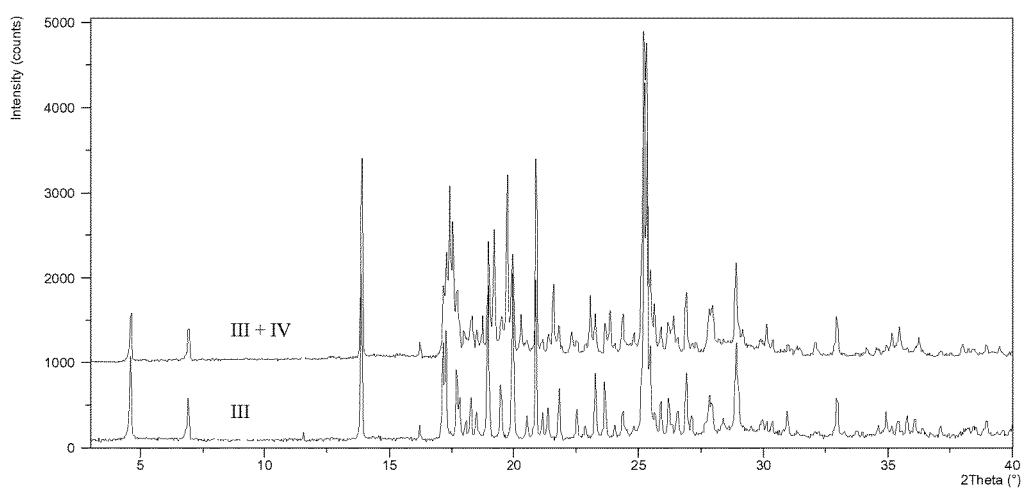
FIG. 7: X-ray powder diffractograms of polymorphic form III (lower curve) and mixture of polymorphic form III and polymorphic form IV (upper curve).
Figure 8:
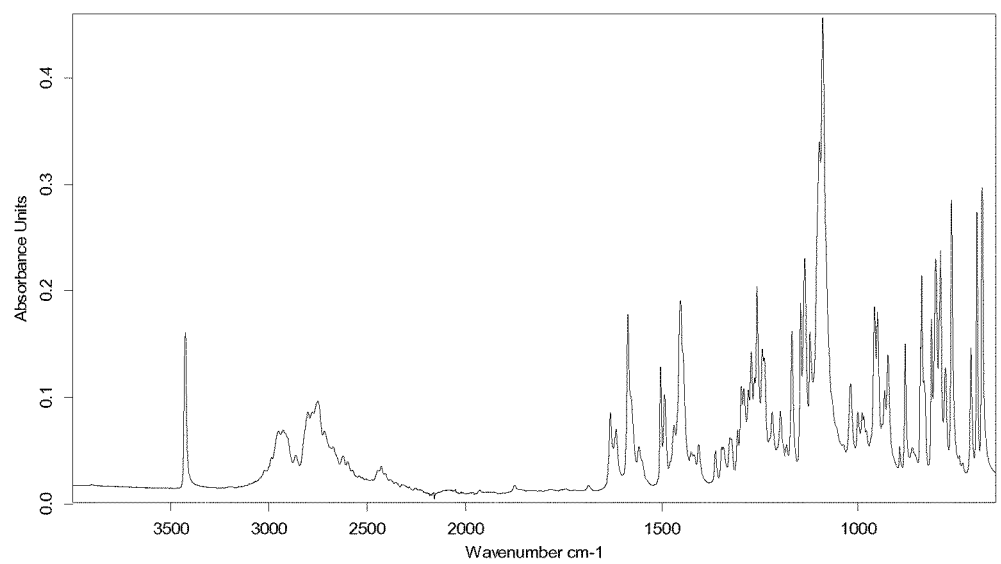
FIG. 8: FTIR spectrum of polymorphic form III
Figure 9:
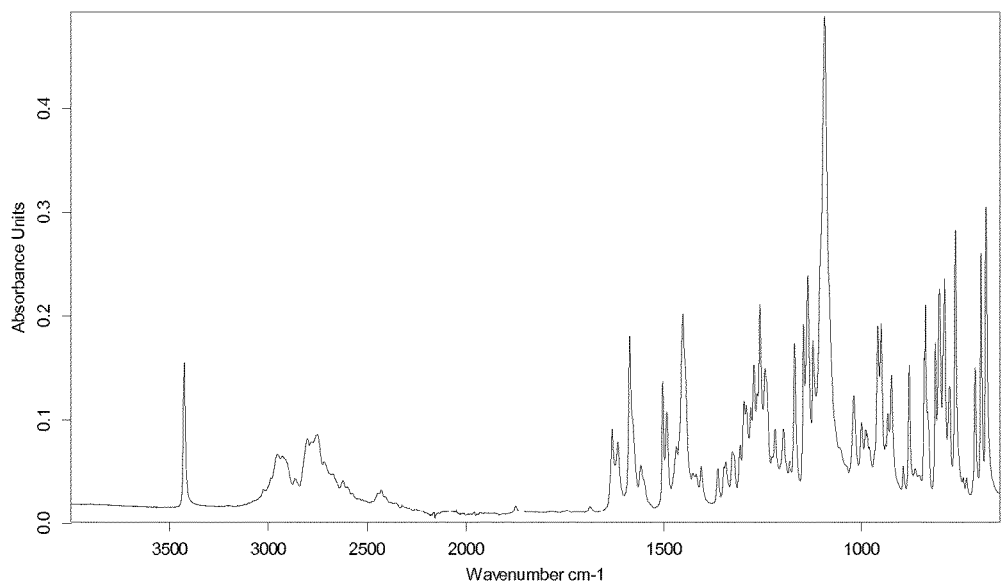
FIG. 9: FTIR spectrum of polymorphic form I

A mixture of polymorphic form III and polymorphic form IV of N-[2-(6-fluoro-1H-indol-3-yl)ethyl]-3-(2,2,3,3-tetrafluoropropoxy)benzylamine hydrochloride was obtained as evaluated by XRPD (FIG. 7).

Characteristic polymorphic form IV XRPD peaks are listed below (±0.10 (° 2θ)):

17.52, 17.73, 19.20, 19.72, 20.30, 21.60, 23.07, 23.87, 26.41

Example 8

FTIR Spectra of Polymorphic Form III and Polymorphic Form I

The IR spectra of polymorphic form I and polymorphic form III were recorded as described above.

TABLE 3

Table 3: FTIR band positions and relative intensity for polymorphic form I and polymorphic form III.

| Band position [cm$^{-1}$] | | |
|---|---|---|
| Polymorphic form I | Polymorphic form III | Relative band intensity |
| 3425 | 3426 | Strong |
| 2951 | 2951 | Medium |
| 2800 | 2800 | Medium |
| 2749 | 2749 | Medium |
| 1631 | 1631 | Medium |
| 1586 | 1586 | Strong |
| 1451 | 1452 | Strong |
| — | 1099 | Shoulder |
| 1092 | 1089 | Very strong |
| 879 | 880 | Medium |
| 762 | 762 | Strong |

The invention claimed is:

1. The polymorphic form III of N-[2-(6-fluoro-1H-indol-3-yl)ethyl]-3-(2,2,3,3-tetrafluoropropoxy)benzylamine hydrochloride, characterized by:
   (A) an X-Ray powder diffractogram showing peaks at the following 2θ-angles: 4.63°, 6.94°, 13.89°, 17.26° and 19.97°; or
   (B) an FTIR spectrum having at least a relatively strong band intensity at the following band positions [cm$^{-1}$]: 3426, 1586, 1089, 762 and a shoulder at 1099 cm$^{-1}$.

2. The polymorphic form III of N-[2-(6-fluoro-1H-indol-3-yl)ethyl]-3-(2,2,3,3-tetrafluoropropoxy)benzylamine hydrochloride according to claim 1, wherein said polymorphic form is characterized by said X-Ray powder diffractogram peaks, wherein said X-Ray powder diffractogram additionally shows peaks at the following 2θ-angles: 18.95°, 22.53° and 23.65°.

3. The polymorphic form III of N-[2-(6-fluoro-1H-indol-3-yl)ethyl]-3-(2,2,3,3-tetrafluoropropoxy)benzylamine hydrochloride according to claim 1, wherein said compound exhibits an X-Ray powder diffractogram as shown in FIG. 5.

4. A process for preparing the polymorphic form III of N-[2-(6-fluoro-1H-indol-3-yl)ethyl]-3-(2,2,3,3-tetrafluoropropoxy)benzylamine hydrochloride comprising:
   (A) stirring a suspension of N-[2-(6-fluoro-1H-indol-3-yl)ethyl]-3-(2,2,3,3-tetrafluoropropoxy)benzylamine hydrochloride in an organic solvent selected from:
      (i) the group consisting of: acetonitrile, proprionitrile, acetone, methanol, ethanol, heptane, toluene, ortho xylene, meta xylene, and para xylene; or
      (ii) a mixture of two or more of said organic solvents;
      at a temperature below 60° C. for at least one week; and
   (B) capturing said polymorphic form III of N-[2-(6-fluoro-1H-indol-3-yl)ethyl]-3-(2,2,3,3-tetrafluoropropoxy)benzylamine hydrochloride.

5. The process according to claim 4, wherein the organic solvent is a mixture of acetone and heptane in the ratio 1:4 or is a mixture of methanol and toluene in the ratio 1:4.

6. The process according to claim 4, wherein said temperature below 60° C. is 45° C.-55° C.

7. The process for preparing the polymorphic form III of N-[2-(6-fluoro-1H-indol-3-yl)ethyl]-3-(2,2,3,3-tetrafluoropropoxy)benzylamine hydrochloride of claim 4, wherein (A) additionally comprises
   adding polymorphic I, form II, amorphous or a mixture of the forms of N-[2-(6-fluoro-1H-indol-3-yl)ethyl]-3-(2,2,3,3-tetrafluoropropoxy)benzylamine hydrochloride to said organic solvent at said temperature below 60° C., to produce a suspension.

8. The process according to claim 7, wherein the organic solvent is a mixture of acetone and heptane in the ratio 1:4 or is a mixture of methanol and toluene in the ratio 1:4.

9. A process for preparing the polymorphic form III of N-[2-(6-fluoro-1H-indol-3-yl)ethyl]-3-(2,2,3,3-tetrafluoropropoxy)benzylamine hydrochloride comprising:
   (A) seeding a suspension of N-[2-(6-fluoro-1H-indol-3-yl)ethyl]-3-(2,2,3,3-tetrafluoropropoxy)benzylamine hydrochloride in an organic solvent selected from:
      (i) the group consisting of: acetonitrile, proprionitrile, acetone, methanol, ethanol, heptane, toluene, ortho xylene, meta xylene, and para xylene; or
      (ii) a mixture of two or more of said organic solvents;
      at a temperature below 60° C., with polymorphic form III of N-[2-(6-fluoro-1H-indol-3-yl)ethyl]-3-(2,2,3,3-tetrafluoropropoxy)benzylamine hydrochloride;
   (B) stirring said seeded suspension for at least two days; and (C) capturing said polymorphic form III of N-[2-(6-fluoro-1H-indol-3yl)ethyl]-3-(2,2,3,3-tetrafluoropropoxy)benzylamine hydrochloride.

10. The process according to claim 9, wherein the organic solvent is a mixture of acetone and heptane in the ratio 1:4 or is a mixture of methanol and toluene in the ratio 1:4.

11. A process for preparing the polymorphic form III of N-[2-(6-fluoro-1H-indol-3-yl)ethyl]-3-(2,2,3,3-tetrafluoropropoxy)benzylamine hydrochloride comprising:
(A) adding polymorphic I, form II, amorphous or a mixture of the forms of N-[2-(6-fluoro-1H-indol-3-yl)ethyl]-3-(2,2,3,3-tetrafluoropropoxy)benzylamine hydrochloride to an organic solvent selected from:
(i) the group consisting of: acetonitrile, proprionitrile, acetone, methanol, ethanol, heptane, toluene, ortho xylene, meta xylene, and para xylene; or
(ii) a mixture of two or more of said organic solvents; at a temperature below 60° C., to produce a suspension; and
(B) seeding with polymorphic form III of N-[2-(6-fluoro-1H-indol-3-yl)ethyl]-3-(2,2,3,3-tetrafluoropropoxy) benzylamine hydrochloride at a temperature below 60° C.; and
(C) capturing polymorphic form III of N-[2-(6-fluoro-1H-indol-3-yl)ethyl]-3-(2,2,3,3-tetrafluoropropoxy)benzylamine hydrochloride.

12. The process according to claim 11, wherein the organic solvent is a mixture of acetone and heptane in the ratio 1:4 or is a mixture of methanol and toluene in the ratio 1:4.

13. A pharmaceutical composition comprising the polymorphic form III of N-[2-(6-fluoro-1H-indol-3-yl)ethyl]-3-(2,2,3,3-tetrafluoropropoxy)benzylamine hydrochloride of claim 1, and a pharmaceutically acceptable carrier or diluent.

14. A pharmaceutical composition comprising the polymorphic form III of N-[2-(6-fluoro-1H-indol-3-yl)ethyl]-3-(2,2,3,3-tetrafluoropropoxy)benzylamine hydrochloride of claim 2, and a pharmaceutically acceptable carrier or diluent.

15. A pharmaceutical composition comprising the polymorphic form III of N-[2-(6-fluoro-1H-indol-3-yl)ethyl]-3-(2,2,3,3-tetrafluoropropoxy)benzylamine hydrochloride of claim 3, and a pharmaceutically acceptable carrier or diluent.

16. A method of treating Alzheimer's disease as adjunctive therapy to acetylcholinesterase treatment comprising administering an effective daily dose of the pharmaceutical composition of claim 13 to a patient in need of such treatment.

17. The method according to claim 16, wherein the effective daily dose administered to the patient of said compound is between about 30 and about 60 mg.

18. A method of treating Alzheimer's disease as adjunctive therapy to acetylcholinesterase treatment comprising administering an effective daily dose of the pharmaceutical composition of claim 14 to a patient in need of such treatment.

19. The method according to claim 18, wherein the effective daily dose administered to the patient of said compound is between about 30 and about 60 mg.

20. A method of treating Alzheimer's disease as adjunctive therapy to acetylcholinesterase treatment comprising administering an effective daily dose of the pharmaceutical composition of claim 15 to a patient in need of such treatment.

21. The method according to claim 20, wherein the effective daily dose administered to the patient of said compound is between about 30 and about 60 mg.

* * * * *